(12) United States Patent
Leighton et al.

(10) Patent No.: US 7,534,905 B2
(45) Date of Patent: May 19, 2009

(54) REAGENTS FOR ASYMMETRIC ALLYLATION, ALDOL, AND TANDEM ALDOL AND ALLYATION REACTIONS

(75) Inventors: James L. Leighton, New York, NY (US); Xiaolun Wang, New York, NY (US); James Kinnaird, Kent (GB)

(73) Assignee: The Trustees of Columbia University In the City of New York, New York, NY (US)

( * ) Notice: Subject to any disclaimer, the term of this patent is extended or adjusted under 35 U.S.C. 154(b) by 314 days.

(21) Appl. No.: 10/504,831

(22) PCT Filed: Mar. 3, 2003

(86) PCT No.: PCT/US03/06308

§ 371 (c)(1),
(2), (4) Date: Jul. 26, 2005

(87) PCT Pub. No.: WO03/074534

PCT Pub. Date: Sep. 12, 2003

(65) Prior Publication Data

US 2005/0288525 A1      Dec. 29, 2005

Related U.S. Application Data

(60) Provisional application No. 60/369,812, filed on Apr. 4, 2002, provisional application No. 60/360,987, filed on Mar. 1, 2002.

(51) Int. Cl.
*C07F 7/10* (2006.01)
*C07F 7/08* (2006.01)
*C07F 7/18* (2006.01)

(52) U.S. Cl. .................. 556/406; 556/407; 556/408; 556/410

(58) Field of Classification Search ................. 556/406, 556/407, 408, 410
See application file for complete search history.

(56) References Cited

OTHER PUBLICATIONS

J. Am. Chem. Soc. 2002, 124, 10672-10673, Aug. 15, 2002.*
Kirupathevy et al; Tetrahedron Asymmetry vol. 5. No. 5, pp. 797-800, 1994; "Chelation Controlled Allylation Of Aldehydes with a Chiral Allylsilylene Derived From (–)-10 Phenylpinanediol".*
Brown et al., Asymmetric carbon-carbon bond formation via B-allyldiisopinocamphenylborane. Simple synthesis of secondary homoallylic alcohols with excellent enantiomeric purities *J. Am. Chem. Soc. 105*:2092-2093 (1983).
Cowden et al., Asymmetric aldol reactions using boron enolates, *Organic Reactions*, vol. 51: 1-191 (1997).
Hafner et al., Enantioselective allyltitanation of aldehydes with cyclopentadienyldialkoxyallyltitanium complexes *J. Am. Chem. Soc. 114*:2321-2336 (1992).
Jadhav et al., Chiral synthesis via orgaonboranes. 5. Asymmetric allylboration with chiral allyldialkylboranes. Synthesis of homoallylic alcohols with exceptionally high enantiomeric excess, *J. Org. Chem. 51*:432-439 (1986).
Jutzi et al., Decamethylsilicocene Chemistry: Reaction with Representative Aldehydes and Ketones, *Organometallics 15*:1930-1934 (1996).
Kinnaird et al., Strained silacycles in organic synthesis: A new reagent for the enantioselective allylation of aldehydes *J. Am. Chem. Soc. 124*:7920-7921 (2002).
Kubota et al., A Highly Practical and Enantioselective Reagent for the Allylation of Aldehydes, *Angew. Chem. Int. Ed. 42*:946-948 (2003).
Patterson et al., Enantioselective aldol condensations: The use of ketone boron enolates with chiral ligands attached to boron *Tet. Lett.. 27*:4787-4790 (1986).
Patterson et al., Aldol reactions of methylketones using chiral boron reagents: A reversal in aldehyde enantioface selectivity *Tet. Lett.. 30*:997-1000 (1989).

(Continued)

*Primary Examiner*—Elvis O Price
(74) *Attorney, Agent, or Firm*—Wilmer Cutler Pickering Hale and Dorr LLP

(57) ABSTRACT

A new class of reagents and method of use of the reagents in the reaction of the reagents with electrophilic compounds. The invention in one embodiment is directed to a method for the formation of an alcohol of the formula (I). The method includes reacting a reagent of the formula (II) with an aldehyde of the formula $R^{10}CHO$ to form the alcohol. $X_3$ is one of O and $C(R^4)(R^5)$. Each of $X_1$ and $X_2$ is independently O or N—R. Each of $C_a$ and $C_b$ is independently an achiral center, an (S) chiral center or an (R) chiral center. $R_a$ and $R_b$ are (i) each independently $C_{1-10}$ alkyl, $C_{6-10}$ aryl or $C_{3-9}$ heteroaryl, or (ii) taken together to form a $C_3$—$C_4$ alkylene chain which together with $C_a$ and $C_b$ forms a 5-membered or 6-membered aliphatic ring. $R_c$ and $R_d$ are each independently hydrogen, $C_{1-10}$ alkyl, $C_{6-10}$ aryl or $C_{3-9}$ heteroaryl. R is $C_{1-10}$ alkyl, $C_{6-10}$ aryl or $C_{3-9}$ heteroaryl. Each of $R^1$, $R^2$, $R^3$, $R^4$, $R^5$ is independently hydrogen, $C_1$—$C_{10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, or halogen. $R^6$ is halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ alkyl-$C_{6-10}$ arylamino, $C_{1-10}$ diarylamino, $OSO_2CF_3$ or SR. $R^{10}$ may be $C_{1-10}$ alkyl, $C_{6-10}$ aryl, or $C_{3-9}$ heteroaryl.

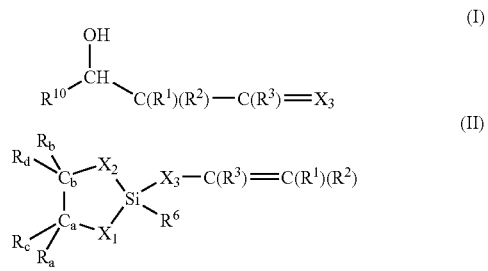

23 Claims, 15 Drawing Sheets

OTHER PUBLICATIONS

Patterson et al., Enantio- and diastereoselective aldol reactions of achiral ethyl and methyl ketones with aldehydes: the use of enol diisopinocampheylborinates *Tetrahedron 46*:4663-4684 (1990).

Racherla et al., Chiral synthesis via orgaonboranes. 27. Remarkably rapid and exceptionally enantioselective (approaching 100% ee) allylboration of representative aldehydes at—100° C. under new salt-free conditions *J. Org. Chem. 56*:401-404 (1991).

Roush et al., Diastereo- and enantioselective aldehyde addition reactions of 2-allyl-1,3,2-dioxaborolane-4,5-dicarboxylic esters, a useful class of tartrate ester modified allylboronates *J. Am. Chem. Soc. 110*:3979-3982 (1988).

Roush et al., N,N-Dibenzyl-N, N-ethylenetartramide: A rationally designed chiral auxiliary for the the allylboration reaction *J. Am. Chem. Soc. 107*:8186-8190 (1985).

Shanmuganathan et al., Chelation controlled allylation of aldehydes with a chiral allylsilene derived from (−)-10-phenylpinanediol, *Tetrahedron: Asymmetry 5*:797-800 (1994).

Wang et al., Asymmetric allylation of aldehydes and glyoxylates through 'C-centered' chiral pentacoordinate allylsilicates or promoted by Lewis Acid, *Chem. Commun.* 2261-2262 (1996).

Wang et al., Asymmetric allylation of aldehydes and glyoxylates through 'C-centered' chiral pentacoordinate allylsilicates or promoted by Lewis Acid, *Tetrahedron Asymmetry 10*:327-338 (1999).

Wang et al., Strained silacycles in organic synthesis: The tandem aldol-allylation reaction, *J. Am. Chem. Soc. 124*:10672-10673 (2002).

Zhang et al., Enantioselective allylation of aldehydes using tartrate ester modified allylsilanes, *Chem. Lett.* 129-130 (1997).

\* cited by examiner

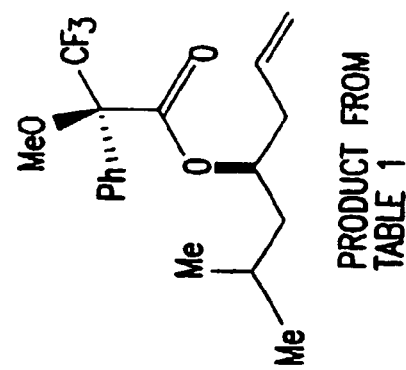
PRODUCT FROM TABLE 1
FIG.6
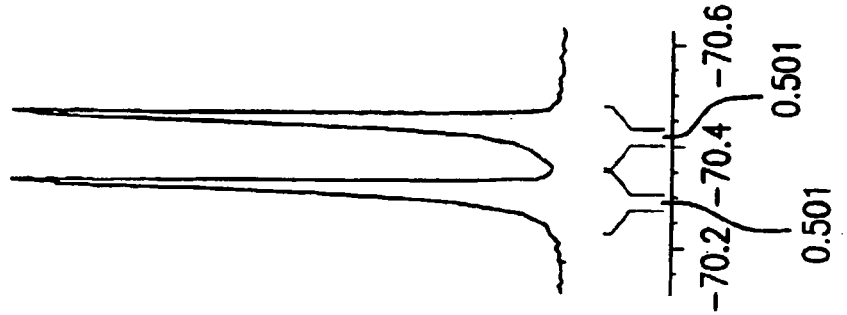
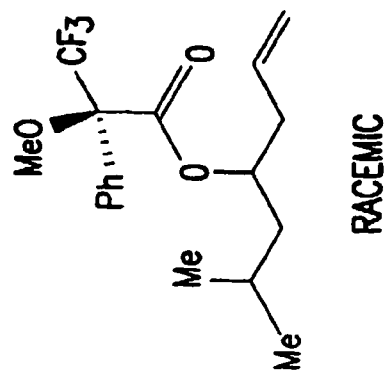
RACEMIC

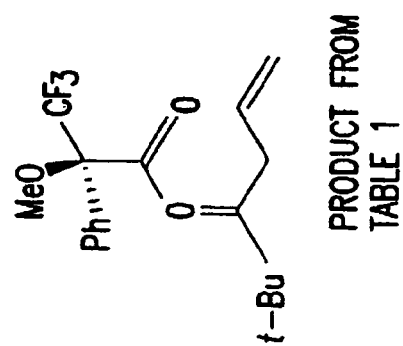
PRODUCT FROM TABLE 1
FIG.8
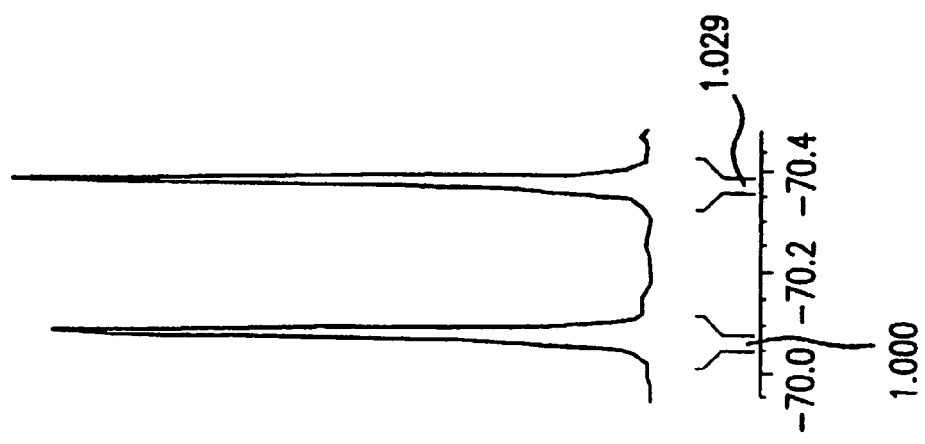
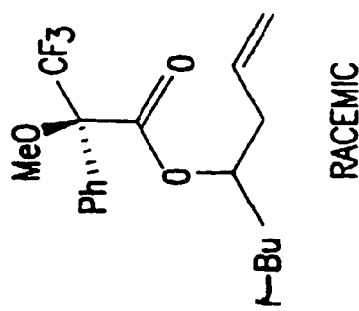
RACEMIC

HPLC CONDITIONS:
CHIRALCEL AD-H, Hex: i-PrOH 500:1, 0.5mL/min.

```
PEAK RetTime TYPE  WIDTH    AREA      AREA
  #   [min]        [min]    mAU *s     %
----+----------+----+------+----------+--------
  1  22.424   VV  0.9291  4312.36816  48.4575
  2  24.854   VB  1.1471  4586.90430  51.5425
```

```
PEAK RetTime TYPE  WIDTH    AREA      AREA
  #   [min]        [min]    mAU *s     %
----+----------+----+------+----------+--------
  1  23.111   PV  0.7682  331.80750   2.5414
  2  24.459   VV  1.3333  1.272243e4  97.4586
```

RACEMIC

REAGENTS FOR ASYMMETRIC ALLYLATION, ALDOL, AND TANDEM ALDOL AND ALLYATION REACTIONS

This application claims priority to the following applications: International Patent Application No. PCT/US03/06308 filed on Mar. 3, 2003 and published under International Publication No. WO 03/074534 on Sep.12, 2003, of which the instant application is a National Stage Filing under 35 U.S.C, § 371, and the provisional applications to which International Patent Application No. PCT/US03/06308 also claims priority, namely, U.S. Provisional Patent Application No. 60/360,987 filed on Mar. 1, 2002 and U.S. Provisional Patent Application No. 60/369,812, filed on Apr. 4, 2002 each of which are incorporated by reference in their entireties herein.

This work was supported by Grant No. GM58133 from the National Institutes of Health (NIH).

FIELD OF THE INVENTION

The present invention relates to reagents which are useful for asymmetric allylations, aldols, and tandem aldol and allylation reactions. In particular, the presente invention relates to cyclic reagents containing a silicon atom which are useful for the preparation by asymmetric allylations, aldols, and tandem aldol and allylation reactions of chiral alcohols and hydrazines.

BACKGROUND OF THE INVENTION

Asymmetric additions of allyl groups and enolates to the carbonyl (C=O) group of aldehydes and to the C=N group of related electrophilic compounds remains one of the most important and fundamental carbonyl addition reactions for the synthesis of optically active chiral compounds containing a chiral carbon center bonded to an oxygen or nitrogen atom. Such compounds may have utility, for example, as pharmaceutically active compounds, or may be used to prepare other pharmaceutically active compounds. Many highly enantioselective allylation reagents and catalysts have been developed, as described, for example, in Brown, H. C. and Jadhav, P. K., J. Am. Chem. Soc., Vol. 105 (1983), p. 2092; Jadhav, P. K., Bhat, K. S., Perumal P. T. and Brown, H. C., J. Org. Chem., Vol. 51 (1986), p. 432; Racherla, U. S. and Brown, H. C., J. Org. Chem., Vol. 56 (1991), p. 401; Roush, W. R., Walts, A. E. and Hoong, L. K., J. Am. Chem. Soc., Vol. 107 (1985), p. 8186; Roush, W. R. and Banfi, W. L., J. Am. Chem. Soc., Vol. 110 (1988), p. 3979; Hafner, A., Duthaler R. O., Marti, R., Ribs, G., Rothe-Streit, P. and Schwarzenbach, F., J. Am. Chem. Soc., Vol. 114 (1992), p. 2321; Wang, Z., Wang, D. and Sui, X., Chem. Commun. (1996), p. 2261; Wang, D., Wang, Z. G., Wang, M. W., Chen, Y. J., Liu, L. and Zhu, Y., Tetrahedron: Asymmetry, Vol. 10 (1999), p. 327; Zhang, L. C., Sakurai, H. and Kira, M., Chem. Lett. (1997), p. 129. Similarly, highly enantioselective enolate reagents have been developed, as described, for example, in Paterson, I., Lister, M. A. and McClure, C. K., Tetrahedron Lett., vol. 27, (1986), p. 4787; Paterson, I. and Goodman, J. M., Tetrahedron Lett., vol. 30, (1989), p. 997; Paterson, I.,Goodman, J. M., Lister, M. A., Schumann, R. C., McClure, C. K. and Norcross, R. D., Tetrahedron, Vol. 46, (1990), p. 4663; and Cowden, C. J. and Paterson, I., Org. React. Vol. 51, (1997), p. 1.

However, several problems have been found to be associated with the allylation and enolate reagents and catalysts of the prior art, including the expense of preparation, the instability of the reagents or the catalysts, the need for using the reagents or the catalysts in situ or shortly after their preparation, the toxicity of the reagents and the byproducts of the reactions of the reagents and the catalysts with aldehydes, and the ease of separation and purification of the reaction products. A generally applicable method for the allylation and the addition of enolates to aldehydes and related electrophilic compounds requires easily and inexpensively formed, stable, and storable reagents and catalysts, reagents and byproducts having little or no toxicity, and easy separation and purification of the products formed. A method combining all these characteristics has until now proven elusive.

SUMMARY OF THE INVENTION

In accordance with the present invention, there is provided a new class of reagents and method of use of the reagents that solves the above-described problems of the prior art, and there is further provided excellent enantioselectivities in the reaction of the reagents with electrophilic compounds.

The invention in a first embodiment is a method for the formation of an allylation reagent of formula

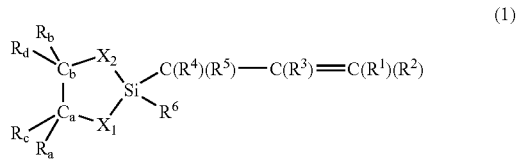

(1)

The method includes reacting a silane of formula

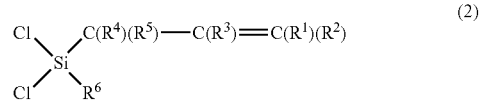

(2)

with a compound of formula

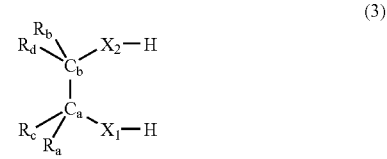

(3)

to form the allylation reagent of formula (1). Each of $X_1$ and $X_2$ is independently O or N—R. Each of $C_a$ and $C_b$ is independently an achiral center, an (S) chiral center or an (R) chiral center. $R_a$ and $R_b$ are (i) each independently $C_{1-10}$ alkyl, $C_{6-10}$ aryl or $C_{3-9}$ heteroaryl, or (ii) taken together to form a $C_3$-$C_4$ alkylene chain which together with $C_a$ and $C_b$ forms a 5-membered or 6-membered aliphatic ring. $R_c$ and $R_d$ are each independently hydrogen, $C_{1-10}$ alkyl, $C_{6-10}$ aryl or $C_{3-9}$ heteroaryl. $R^6$ of formulas (1) and (2) is a halogen, hydrogen, $C_{1-10}$ alkyl, $C_{6-10}$ aryl, $C_{3-9}$ heteroaryl, $C_{1-10}$ dialkylamino, $C_{1-10}$ alkyl-$C_{6-10}$ arylamino, $C_{1-10}$ diarylamino, or SR. R is $C_{1-10}$ alkyl, $C_{6-10}$ aryl or $C_{3-9}$ heteroaryl. Each of $R^1$, $R^2$, $R^3$, $R^4$, $R^5$ of formulas (1) and (2) is independently hydrogen, $C_1$-$C_{10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, or halogen.

The invention in another embodiment is a reagent of formula (4)

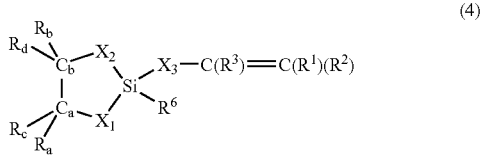

where $X_3$ is one of O and $C(R^4)(R^5)$ and $X_1$, $X_2$, $C_a$, $C_b$, R, $R_a$, $R_b$, $R_c R_d$, $R^1$, $R^2$, $R^3$, $R^4$, $R^5$ are as defined above in connection with formulas (1) and (2). $R^6$ in formula (4) is halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, $-O-C(R^9)=C(R^7)(R^8)$, $OSO_2CF_3$ or SR. Each of $R^7$, $R^8$ and $R^9$ are defined in the same way as $R^1$, $R^2$, $R^3$, $R^4$, and $R^5$ in connection with formulas (1) and (2).

The invention in another embodiment is a method for the formation of a first reagent of formula (5)

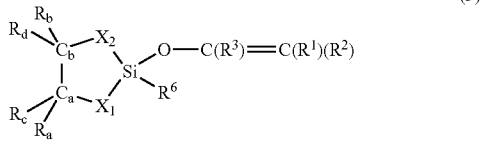

The method includes reacting a second reagent of formula (6)

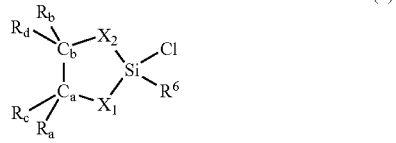

with one equivalent of a lithium enolate of the formula $Li-O-C(R^3)=C(R^1)(R^2)$ to form the first reagent. Each of $X_1$ and $X_2$ is independently O or N—R. Each of $C_a$ and $C_b$ is independently an achiral center, an (S) chiral center or an (R) chiral center. $R_a$ and $R_b$ are (i) each independently $C_{1-10}$ alkyl, $C_{6-10}$ aryl or $C_{3-9}$ heteroaryl, or (ii) taken together to form a $C_3$-$C_4$ alkylene chain which together with $C_a$ and $C_b$ forms a 5-membered or 6-membered aliphatic ring. $R_c$ and $R_d$ are each independently hydrogen, $C_{1-10}$ alkyl, $C_{6-10}$ aryl or $C_{3-9}$ heteroaryl. $R^6$ is a halogen, hydrogen, $C_{1-10}$ alkyl, $C_{6-10}$ aryl, $C_{3-9}$ heteroaryl, $C_{1-10}$ dialkylamino, $C_{1-10}$ alkyl-$C_{6-10}$ arylamino, $C_{1-10}$ diarylamino, $O-C(R^3)=C(R^1)(R^2)$, or SR. R is $C_{1-10}$ alkyl, $C_{6-10}$ aryl or $C_{3-9}$ heteroaryl. Each of $R^1$, $R^2$, and $R^3$, is independently hydrogen, $C_1$-$C_{10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, or halogen.

The invention in another embodiment is a method for the formation of an alcohol of formula (7)

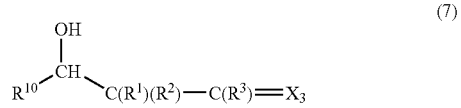

The method includes reacting a reagent of formula (8)

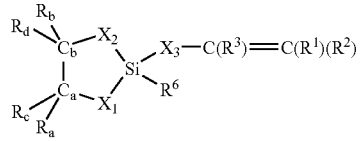

with an aldehyde of formula $R^{10}CHO$ to form the alcohol of formula (7), where $X_3$ is one of O and $C(R^4)(R^5)$ and $X^1$, $X_2$, $C_a$, $C_b$, R, $R_a$, $R_b$, $R_c$, $R_d$, $R^1$,$R^2$, $R^3$, $R^4$, and $R^5$ are as defined above in connection with formulas (1), (2) and (3). $R^6$ is a halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, $OSO_2CF_3$ or SR. $R^{10}$ is $C_{1-10}$ alkyl, $C_{6-10}$ aryl, or $C_{3-9}$ heteroaryl.

The invention in another embodiment is a method for the formation of a compound of formula (9)

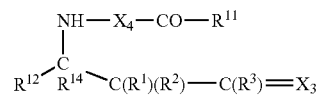

The method includes reacting a reagent of formula (10)

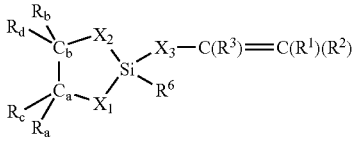

with a compound of the formula $R^{12}C(R^{14})=N-X_4-CO-R^{11}$. $X_3$ is one of O and $C(R^4)(R^5)$. $X_4$ is O or NH. $X^1$, $X_2$, $C_a$, $C_b$, R, $R_a$, $R_b$, $R_c$, $R_d$, $R^1$, $R^2$, $R^3$, $R^4$, and $R^5$ are as defined above in connection with formulas (1), (2) and (3). $R^6$ is a halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{1-10}$ diarylamino, $OSO_2CF_3$ or SR. $R^{11}$ is hydrogen, $C_{1-10}$ alkyl, $C_{6-10}$ aryl, or $C_{3-9}$ heteroaryl, $R^{12}$ is $C_{1-10}$ alkyl, $C_{6-10}$ aryl or $C_{3-9}$ heteroaryl. $R^{14}$ is hydrogen, $C_{1-10}$ alkyl, $C_{6-10}$ aryl, or $C_{3-9}$ heteroaryl.

The invention in another embodiment is a method for the formation of a first allylation reagent of formula (11)

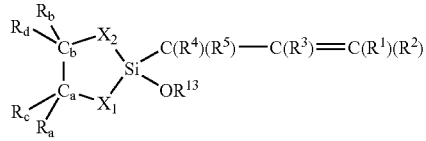

The method includes reacting a second allylation reagent of formula (12)

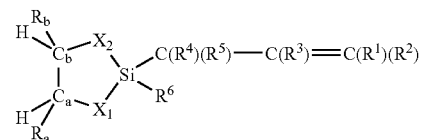

with an alcohol of the formula $H-O-R^{13}$ in the presence of a base to form the first allylation reagent of formula (11). $X^1$, $X_2$, $C_a$, $C_b$, R, $R_a$, $R_b$, $R_c$, $R_d$, $R^1$, $R^2$, $R^3$, $R^4$, and $R^5$, are as defined above in connection with formulas (1), (2) and (3). $R^6$ is a halogen or $OSO_2CF_3$. $R^{13}$ is $C_1$-$C_{10}$ alkyl, $C_{6-10}$ aryl, or $C_{3-9}$ heteroaryl.

The invention in another embodiment is a method for the formation of a first allylation reagent of formula (13)

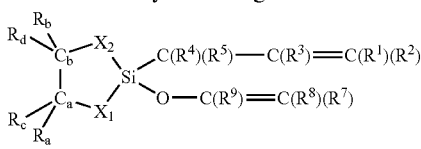

The method includes reacting a second allylation reagent of formula (14)

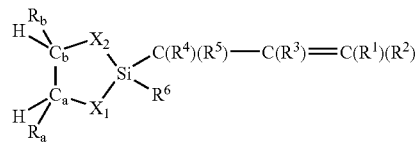

with a lithium enolate of the formula Li—O—C(R$^9$)=C(R$^7$)(R$^8$) to form the first allylation reagent. X$^1$, X$_2$, C$_a$, C$_b$, R, R$_a$, R$_b$, R$_c$, R$_d$, R$^1$, R$^2$, R$^3$, R$^4$, R$^5$, R$^7$, R$^8$ and R$^9$ are as defined above in connection with formulas (1), (2) and (3). R$^6$ is a halogen or OSO$_2$CF$_3$.

The invention in another embodiment is a method for the formation of a first reagent of formula (15)

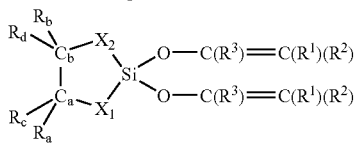

The method includes reacting a second reagent of formula (16)

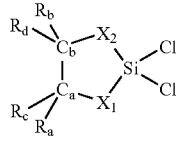

with two equivalents of a lithium enolate of the formula Li—O—C(R$^3$)=C(R$^1$)(R$^2$) to form the first reagent of formula (15). X$_1$, X$_2$ and R are as defined above in connection with formulas (1), (2) and (3). Each of C$_a$ and C$_b$ is independently an achiral center, an (S) chiral center or an (R) chiral center. R$_a$ and R$_b$ are (i) each independently C$_{1-10}$ alkyl, C$_{6-10}$ aryl or C$_{3-9}$ heteroaryl, or (ii) taken together to form a C$_3$-C$_4$ alkylene chain which together with C$_a$ and C$_b$ forms a 5-membered or 6-membered aliphatic ring. R$_c$ and R$_d$ are each independently hydrogen, C$_{1-10}$ alkyl, C$_{6-10}$ aryl or C$_{3-9}$ heteroaryl. Each of R$^1$, R$^2$, and R$^3$, is independently hydrogen, C$_1$-C$_{10}$ alkyl, C$_{6-10}$ aryl, C$_{3-9}$ heteroaryl, C$_{1-10}$ alkoxy, C$_{6-10}$ aryloxy, C$_{1-10}$ dialkylamino, C$_{1-10}$ alkyl-C$_{6-10}$ arylamino, C$_{1-10}$ diarylamino, or halogen.

The invention in another embodiment is a method for the formation of a diol of formula (17)

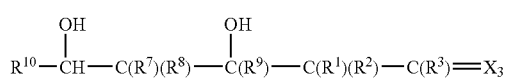

The method includes reacting a reagent of formula (18)

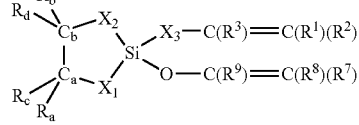

with an aldehyde of formula R$^{10}$CHO to form the diol of formula (17). X$_3$ is one of O and C(R$^4$)(R$^5$). X$^1$, X$_2$, C$_a$, C$_b$, R, R$_a$, R$_b$, R$_c$, R$_d$, R$^1$, R$^2$, R$^3$, R$^4$, R$^5$, R$^7$, R$^8$ and R$^9$ are as defined above in connection with formulas (1), (2), (3) and (4). R$^{10}$ is C$_{1-10}$ alkyl, C$_{6-10}$ aryl, or C$_{3-9}$ heteroaryl.

The invention in another embodiment is a method for the formation of a compound of formula (19)

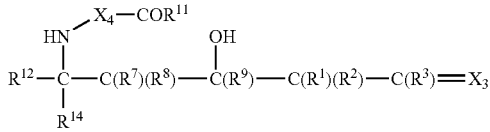

The method includes reacting a reagent of formula (20)

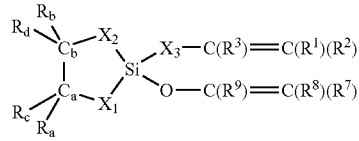

with a compound of the formula R$^{12}$C(R$^{14}$)=N—X$_4$—CO—R$^{11}$ to obtain the compound of formula (19). X$_3$ is one of O and C(R$^4$)(R$^5$). X$_4$ is one of NH and O. X$^1$, X$_2$, C$_a$, C$_b$, R, R$_a$, R$_b$, R$_c$. R$_d$, R$^1$, R$^2$, R$^3$, R$^4$, R$^5$, R$^7$, R$^8$ and R$^9$ are as defined above in connection with formulas (1), (2), (3) and (4). R$^{11}$ is hydrogen, C$_{1-10}$ alkyl, C$_{6-10}$ aryl, or C$_{3-9}$ heteroaryl. R$^{12}$ is C$_{1-10}$ alkyl, C$_{6-10}$ aryl or C$_{3-9}$ heteroaryl. R$^{14}$ is hydrogen, C$_{1-10}$ alkyl, C$_{6-10}$ aryl, or C$_{3-9}$ heteroaryl.

In the foregoing formulas (1)-(20), the double bond between C(R$^3$) and C(R$^1$)(R$^2$), the double bond between X and C(R$^3$), and the double bond between C(R$^9$) and C(R$^8$)(R$^7$) may each be an (E) double bond, a (Z) double bond, or a double bond that does not exhibit (E)/(Z) isomerism. In the compound of the formula R$^{12}$C(R$^{14}$)=N—X$_4$—CO—R$^{11}$, the double bond between C and N may be an (E) double bond or a (Z) double bond.

BRIEF DESCRIPTION OF THE FIGURES

FIG. 6 shows a $^{19}$F NMR (C$_6$D$_6$, 282 MHz) spectrum of the Mosher ester of the alcohol obtained by allylation of isovaleraldehyde with allylation reagent 3 and of the corresponding racemic alcohol.

FIG. 8 shows a $^{19}$F NMR ($C_6D_6$, 282 MHz) spectrum of the Mosher ester of the alcohol obtained by allylation of pivaldehyde with allylation reagent 3 and of the corresponding racemic alcohol.

DETAILED DESCRIPTION OF THE INVENTION

Figure 1:
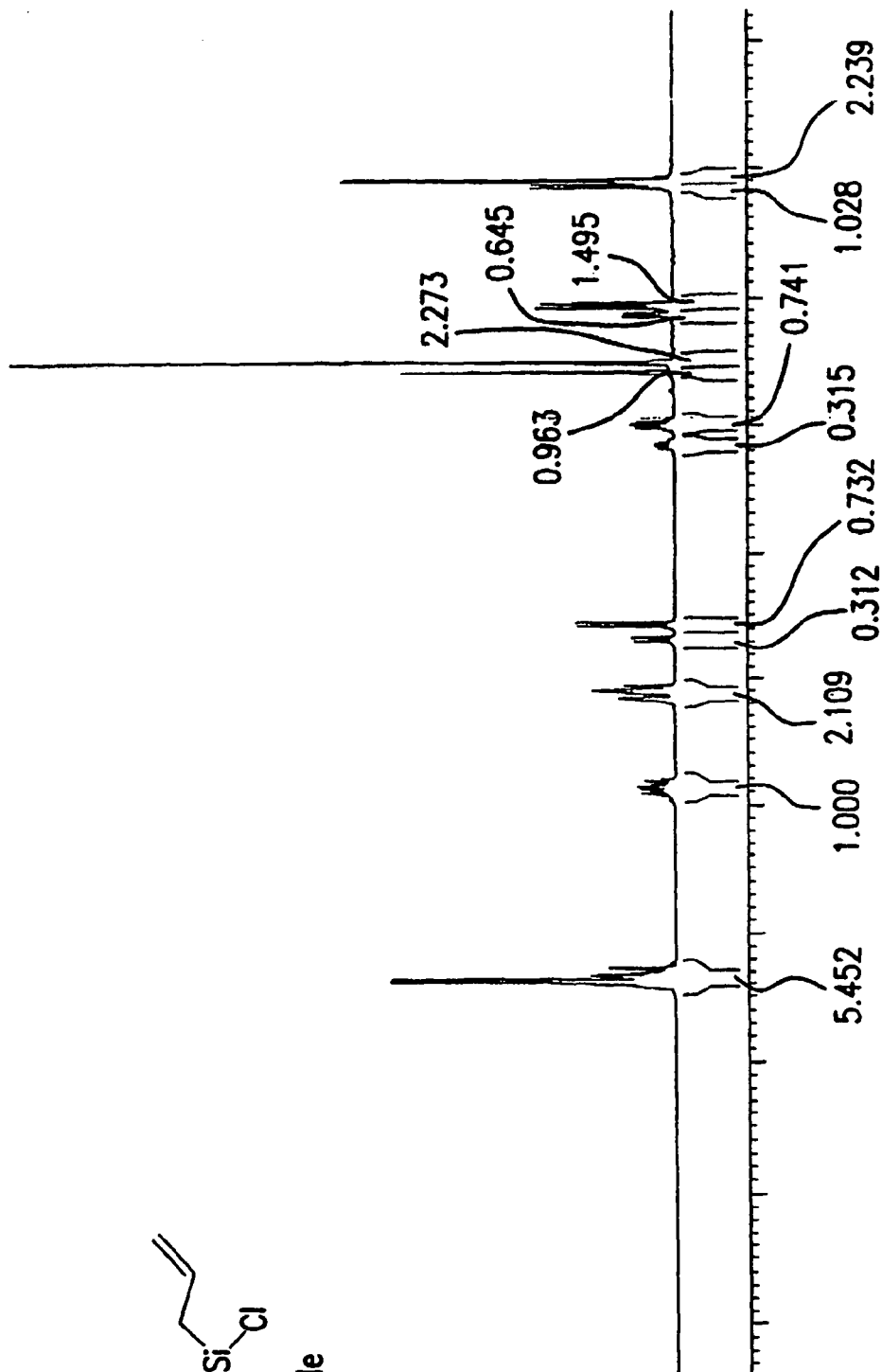
FIG. 1 shows the $^1$H NMR spectrum of allylation reagent 3.
Figure 1:
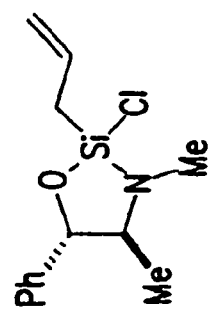

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently $C_1$-$C_{10}$ alkyl, $C_1$-$C_{10}$ alkoxy, $C_{6-10}$ aryl, $C_{3-9}$ heteroaryl, $C_{6-10}$ aryloxy, $C_1$-$C_{10}$ dialkylamino, or silyloxy in which the silicon has three substituents, where each substituent is independently hydrogen, $C_{1-10}$ alkyl, $C_{6-10}$ aryl or $C_{3-9}$ heteroaryl, or halogen. The alkyl group may contain one or more carbon-carbon double bonds, one or more carbon-carbon triple bonds, or a combination thereof Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbomyl, methoxymethyl, phenylmethyl, 4-bromophenylmethyl, 4-methoxyphenylmethyl, phenoxymethyl, dimethylaminomethyl, chloromethyl, 2-phenylethyl, (E)- and (Z)-2-phenylethenyl (Ph-CH=CH—), benzyloxymethyl, and the like.

The term "halogen", as used herein, means chlorine (Cl), fluorine (F), iodine (I) or bromine (Br).

The term "alkoxy", as used herein, means "alkyl-O—", wherein "alkyl" is defined as above and O represents oxygen. Examples of "alkoxy" groups include methoxy, ethoxy, n-butoxy, tert-butoxy, and alkoxy groups in which the alkyl group is halogenated, such as alkoxy groups in which the alkyl group is fluorinated, including, for example, trifluoroethoxy and 1-trifluoromethyl-2-trifluoroethoxy.

The term "alkylthio", as used herein, means "alkyl-S—", wherein "alkyl" is defined as above and S represents sulfur. Examples of "alkylthio" groups include methylthio, ethylthio, n-butylthio, and tert-butylthio.

The term "aryl", as used herein, unless otherwise indicated, includes an organic radical obtained from an aromatic hydrocarbon by removal of one hydrogen from a carbon of the aromatic hydrocarbon, wherein the radical is optionally substituted at between one and three carbons with a substituent at each carbon, where the substituent at each carbon is independently $C_1$-$C_{10}$ alkyl, $C_1$-$C_{10}$ alkoxy, $C_{6-10}$ aryl, $C_{6-10}$ aryloxy, $C_1$-$C_{10}$ dialkylamino, or halogen. Examples of "aryl" groups include phenyl, 1-naphthyl, 2-naphthyl, o-, m-, and p-methylphenyl, o-, m-, and p-methoxyphenyl, o-, m-, and p-diphenyl, o-, m-, and p-phenoxyphenyl, and o-, m-, and p-chlorophenyl.

The term "heteroaryl", as used herein, unless otherwise indicated, includes an organic radical obtained from a heteroaromatic hydrocarbon having a heteroaromatic ring and one or two heteroatoms in the heteroaromatic ring by removal of one hydrogen from a carbon of the heteroaromatic hydrocarbon, wherein one or two heteroatoms are selected from the group consisting of O, N and S the radical is optionally substituted at between one and three carbons, at the one or two heteroatoms, or at a combination thereof with a substituent at each carbon, heteroatom or combination thereof, where the substituent is independently $C_1$-$C_{10}$ alkyl, $C_1$-$C_{10}$ alkoxy, $C_{6-10}$ aryl, $C_{6-10}$ aryloxy, $C_1$-$C_{10}$ dialkylamino, $C_{10}$ alkoxycarbonyl, or halogen. Examples of "heteroaryl" groups include 2-furyl, 3-furyl, 2-thiophenyl, 3-indolyl, 3-(N-t-butoxycarbonyl)-indolyl, 2-pyridyl, 3-pyridyl, 2-chloro-5-pyridyl, 2-pyrrolyl and 2-(N-t-butoxycarbonyl)-pyrrolyl.

The term "aryloxy", as used herein, means "aryl-O—", wherein "aryl" is defined as above and O represents oxygen. Examples of "aryloxy" groups include phenoxy, 1-naphthoxy, and 2-naphthoxy.

The term "dialkylamino", as used herein, means "alkyl-N-alkyl", wherein "alkyl" is defined as above and N represents nitrogen. The two alkyl groups in the dialkylamino group may be the same or different. The term "$C_{1-10}$ dialkylamino" as used herein is intended to denote a dialkylamino group in which each of the two alkyl groups is a $C_{1-10}$ alkyl group. Examples of "dialkylamino" groups include dimethylamino, diethylamino, and ethylmethylamino.

The term "alkylarylamino", as used herein, means "alkyl-N-aryl", wherein "alkyl" and "aryl" are defined above and N represents nitrogen. The term "$C_{1-10}$ alkyl-$C_{6-10}$ arylamino" as used herein is intended to denote an alkylarylamino group in which the alkyl group is a $C_{1-10}$ alkyl group and the aryl group is a $C_{6-10}$ aryl group. An example of "alkylarylamino" group is methylphenylamino.

The term "diarylamino", as used herein, means "aryl-N-aryl", wherein "aryl" is defined as above and N represents nitrogen. The two aryl groups may be the same or different. The term "$C_{6-10}$ diarylamino" as used herein is intended to denote a diarylamino group in which each of the two aryl groups is a $C_{6-10}$ aryl group. An example of a "diarylamino" group is diphenylamino.

The term "alkylene chain" as used herein, unless otherwise indicated, refers to a monovalent aliphatic hydrocarbon diradical having a straight chain, branched chain, monocyclic, or polycyclic moiety or combinations thereof, wherein the diradical is optionally substituted at one or more carbons with one or more substituents at each carbon, where the one or more substituents are independently $C_1$-$C_{10}$ alkyl, $C_1$-$C_{10}$ alkoxy, $C_{6-10}$ aryl, $C_{6-10}$ aryloxy, $C_1$-$C_{10}$ dialkylamino, or halogen. The alkylene chain may contain one or more carbon-carbon double bonds. Examples of alkylene chains include —$CH_2$—$CH_2$—$CH_2$—, —$CH_2$—$CH_2$—$CH_2$—$CH_2$—, and —$CH_2$—CH=CH—$CH_2$—.

The term "base" as used herein, unless otherwise indicated, refers to a compound capable of removing a proton from an acidic group such as an —OH group. Exemplary bases include mono-, di-, and trialkylamines, such as, for example, diazabicycloundecene (DBU), diazabicyclononene (DBN) and triethylamine.

Exemplary silanes which may react with compounds of formula (3) according to the method of the invention include allyltrichlorosilane, allylmethyldichlorosilane, allylphenyl-dichlorosilane, and silanes having the formula $CH_2$=CH—$CH_2SiCl_2Y$, where Y=I, Br, F, $OSO_2CF_3$, $C_{1-10}$ alkoxy, $C_{6-10}$ aryloxy, $C_{1-10}$ dialkylamino, or $C_{1-10}$ alkylthio.

In an exemplary embodiment of the invention, $C_a$ and $C_b$ are achiral centers in the compound of the formula (3) and the reagents of the invention are achiral compounds. In this embodiment, the diols formed from the reagents of the invention according to the method of the invention are formed diastereoselectively.

In another exemplary embodiment of the invention, $C_a$ and $C_b$ are chiral centers in the compound of the formula (3) and the reagents of the invention are chiral compounds. In this embodiment, the homoallylic alcohols and the diols formed from the reagents of the invention according to the method of the invention are formed enantioselectively, and the diols are also formed diastereoselectively. As used herein, the term "enantioselectively" refers to forming a first of two enantiomers in an amount in excess of the second enantiomer. As used herein, the term "diastereoselectively" refers to forming a first of two or more diastereomers an amount in excess of the remaining diastereomer or diastereomers. The term "enantiomeric excess" denotes the amount by which the first enantiomer is in excess of the second enantiomer. The term "diastereomeric excess" denotes the amount by which the first diastereomer is in excess of the remaining diastereomer or diastereomers.

The compounds of formula (3) may include, for example, compounds in which $R_a$ and $R_b$ are independently methyl or phenyl, and in which $R_c$ and $R_d$ are independently methyl or hydrogen. For example, the compounds of formula (3) include aminoalcohols (1S, 2S)-pseudoephedrine, (1R, 2R)-pseudoephedrine. The compounds of formula (3) also include the aminoalcohols shown in Chart 1, which may react with, for example, allyltrichlorosilane to give the corresponding reagents.

Chart 1

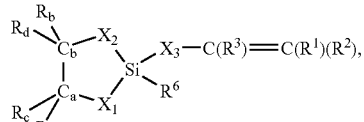

Exemplary aminoalcohols further include compounds of the formula (3) in which each of $R_a$ and $R_b$ is independently methyl or phenyl, $X_2$=O and $X_1$=NR, where R is methyl, benzyl, or phenyl.

Exemplary compounds of formula (3) also include diols, including pinacol (($CH_3)_2COH)_2$ and chiral diols such as, for example, diol 28, having the following formula:

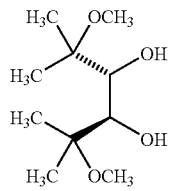

28

Reaction of 28 with allyltrichlorosilane leads to the formation of chiral reagent 29, as shown in the following equation.

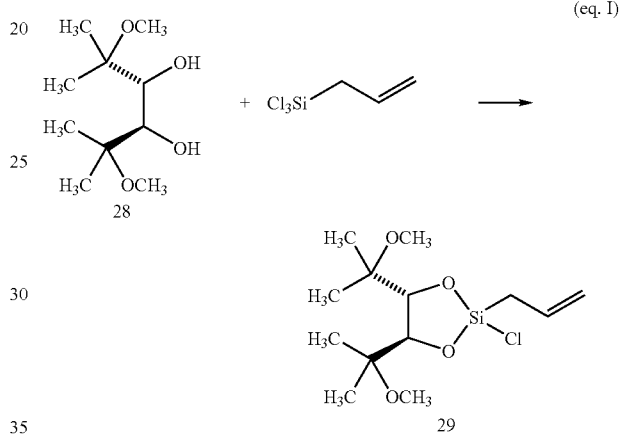

(eq. I)

The compounds of formula (3) also include, for example, compounds in which $R_a$ and $R_b$ taken together form a $C_4$ alkylene chain which together with $C_a$ and $C_b$ forms a 6-membered aliphatic ring. For example, compounds of formula (3) include the diamine (1R,2R)-N,N-Dibenzyl-cyclohexane-1, 2-diamine.

In one embodiment, the reaction between the silane and the compound of formula (3) takes place in the absence of a catalyst. The reaction may also take place in the absence of an additional reagent. In another embodiment, the reaction between the silane and the compound of formula I takes place in the presence of a catalyst.

In an exemplary embodiment of the invention, in the reagent having the formula (10)

(10)

$$R_d\underset{R_c}{\overset{R_b}{\diagdown}}\underset{\underset{R_a}{|}}{C_b}\underset{X_1}{\overset{X_2}{\diagdown}}\underset{R^6}{\overset{|}{Si}}-X_3-C(R^3)=C(R^1)(R^2),$$

$X_3$=C($R^4$)($R^5$) and the reagent is an allylation reagent. The allylation reagent may be a stable compound which does not decompose when stored at a temperature lower or equal to 25° C. for a period of time of up to several weeks, such as, for example, a period of time of two months.

As an example, when allyltrichlorosilane was treated with the diol pinacol and 1,8-diazabicyclo[5.4.0]undec-7-ene (DBU) in $CH_2Cl_2$, allylation reagent 1 was formed in accordance with Scheme 1. Compound 1 was purified by distillation and obtained with 70% yield.

As another example, the reaction of the aminoalcohol (1S, 2S)-pseudoephedrine with allyltrichlorosilane and Et$_3$N in CH$_2$Cl$_2$ allowed the isolation of chiral allylation reagent 3 as an approximately 2:1 mixture of diastereomers with 88% yield, as shown in Scheme 1. 3 may be purified by distillation. Reagent 3 is stable and may be stored for several weeks without appreciable decomposition. The $^1$H NMR spectrum of reagent 3, which is shown in FIG. 1, is in agreement with the structure of reagent 3.

Reagent 3 is available in both enantiomeric form, which may be obtained by reaction with allyltrichlorosilane of (1S, 2S)-pseudoephedrine and of (1R,2R)-pseudoephedrine, respectively, both of which are inexpensive starting materials.

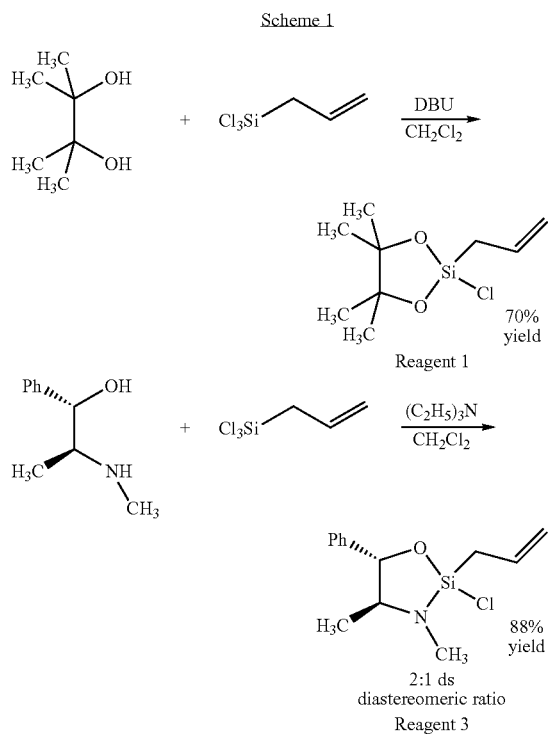

The reaction between the reagent having formula (8)

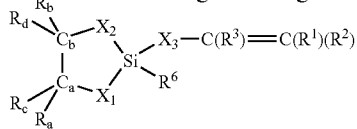

and the aldehyde R$^{10}$CHO may be performed using a solvent which may be, for example, toluene, tetrahydrofuran (THF), N,N-dimethylformamide (DMF), ethyl acetate (EtOAc), dichloromethane (CH$_2$Cl$_2$), hexane, t-butyl methyl ether (t-BuOMe), diethyl ether (Et$_2$O), acetonitrile (CH$_3$CN), and benzene. In a preferred embodiment, the solvent is toluene. In an exemplary embodiment, the concentration of the aldehyde in the solvent may range from 0.05 M to 0.5 M. For example, a concentration of about 0.2 M aldehyde may be used. In another exemplary embodiment, the reaction may be performed in the absence of solvent.

The reaction may be performed at a temperature ranging from about −78° C. to about 25° C. In a preferred embodiment, the temperature is about −10° C. The reaction is preferably performed in the absence of a catalyst.

The group R$^{10}$ in the aldehyde, which is a C$_{1-10}$ alkyl or C$_{6-10}$ aryl group, may be, for example, a methyl group, a t-butyl group, or a phenyl group.

When the reagent is an allylation reagent (X═C(R$^4$)(R$^5$)), the product of the reaction is a homoallylic alcohol. As an example, the reaction of reagent 1 with benzaldehyde (R$^{10}$═phenyl) gave alcohol 2, as shown in Scheme 2, in racemic form. The reaction of reagent 3 with benzaldehyde in benzene at room temperature gave the S enantiomer of alcohol 2 (2(S)) with 81% enantiomeric excess (ee), in accordance with Scheme 2.

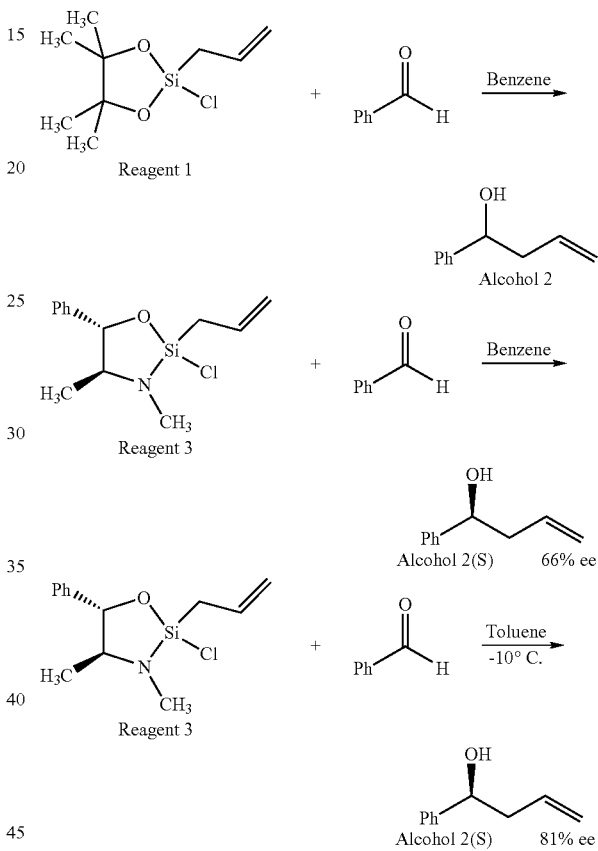

Reagent 3 may be reacted with several other exemplary aldehydes, as shown in Scheme 3. Thus, for example, dihydrocinnamaldehyde was allylated to give alcohol 4(R) with 88% ee, cinnamaldehyde to give alcohol 5(S) with 78% ee, benzyloxyacetaldehyde to give alcohol 6(S) with 88% ee and cyclohexanecarboxaldehyde to give alcohol 7(S) with 86% ee. In each case, the chiral alcohol is readily isolated upon completion of the allylation reaction, which typically requires about 12-16 hours, by adding 1 M HCl and ethyl acetate to the reaction mixture. The resulting mixture is stirred for 15 minutes. An aqueous phase and an organic phase are formed. The aqueous phase and the organic phase are separated. The organic phase is then concentrated to give the chiral alcohol. The pseudoephedrine originally used to form reagent 3 according to Scheme 2 is regenerated upon addition of the 1 M HCl, and remains in the aqueous phase after the aqueous phase and the organic phase are separated. The pseudoephedrine may be recovered from the aqueous phase and used to prepare additional amounts of reagent 3.

Figure 3:
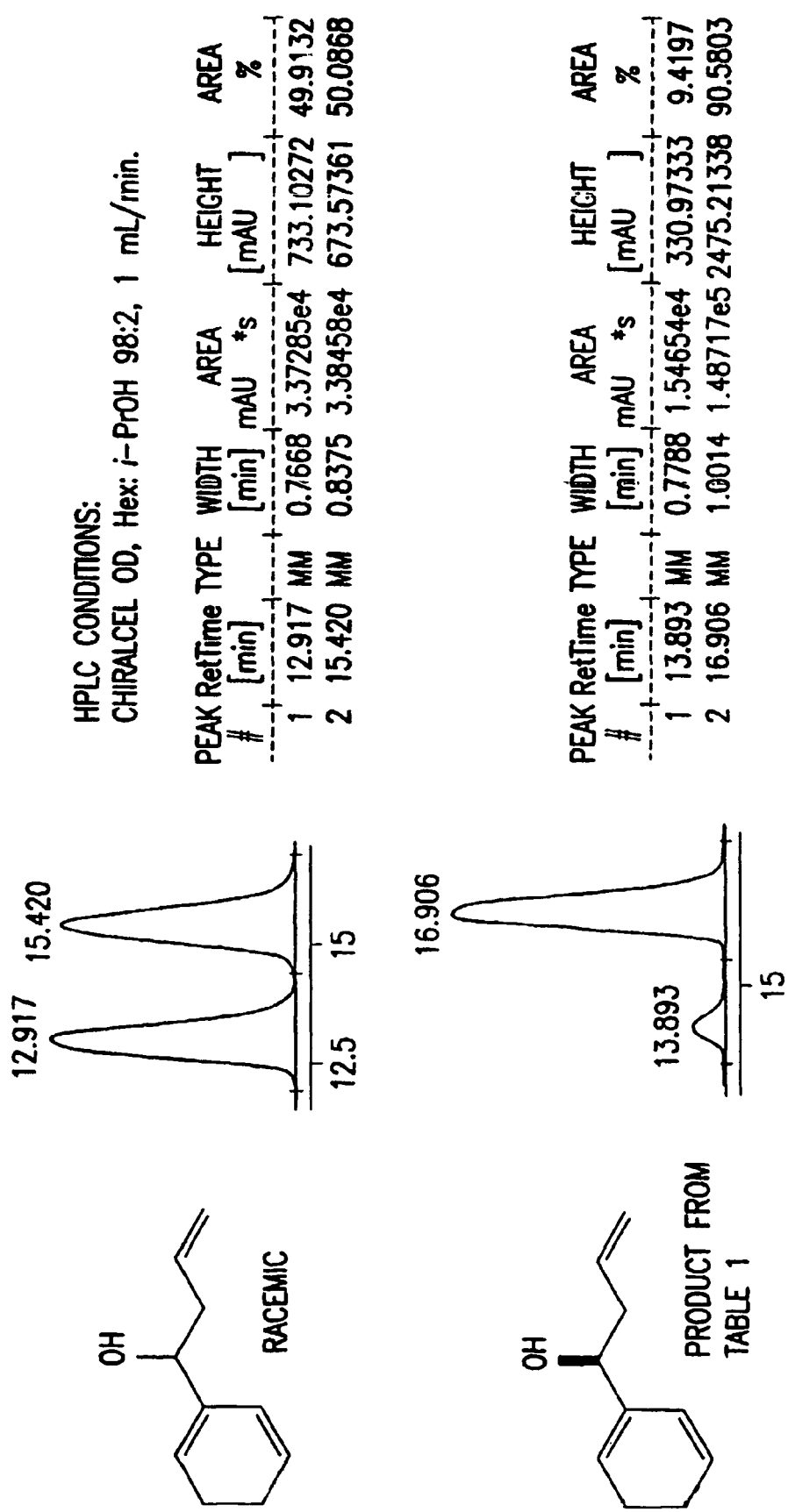
FIG. 3 shows a chiral HPLC analysis of the alcohol obtained by allylation of benzaldehyde with allylation reagent 3 and of the corresponding racemic alcohol.
Figure 4:
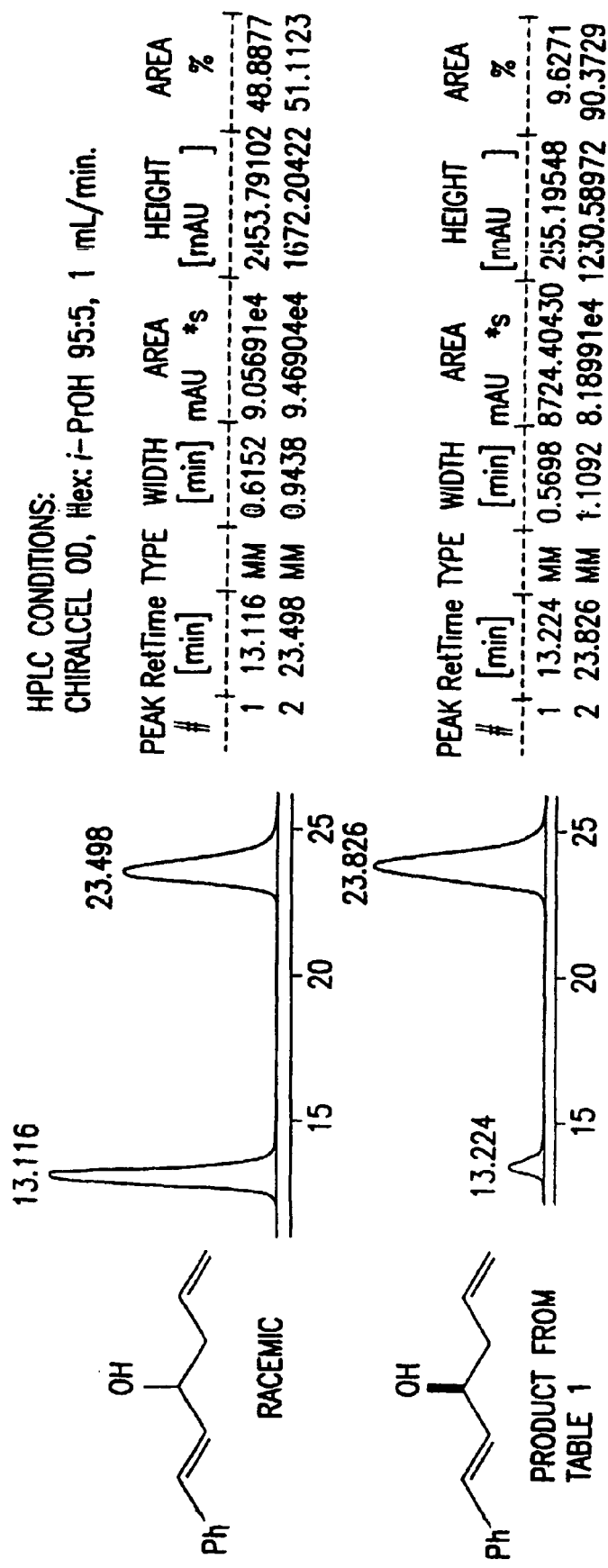
FIG. 4 shows a chiral HPLC analysis of the alcohol obtained by allylation of cinnamaldehyde with allylation reagent 3 and of the corresponding racemic alcohol.
Figure 5:
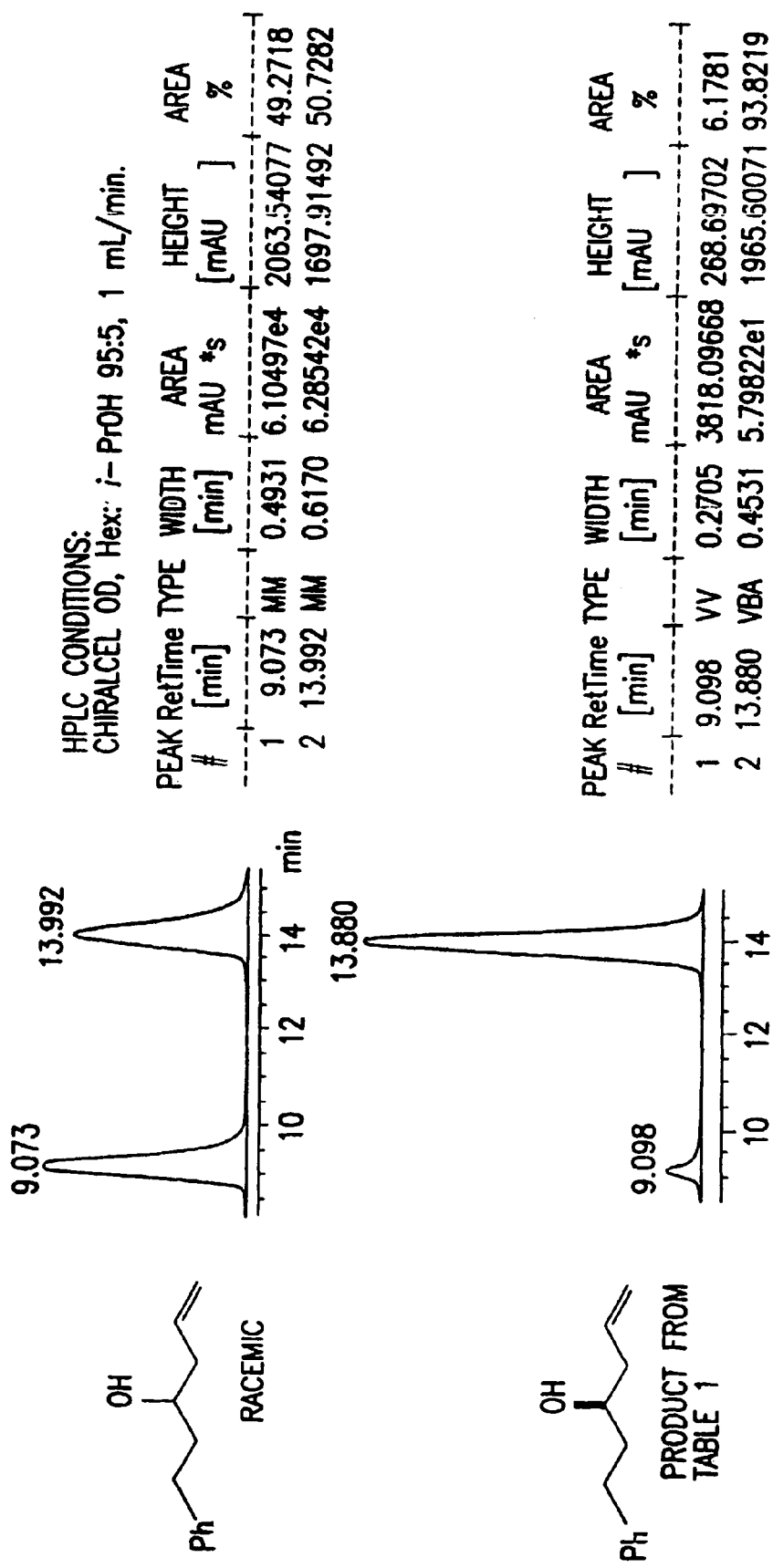
FIG. 5 shows a chiral HPLC analysis of the alcohol obtained by allylation of dihydrocinnamaldehyde with allylation reagent 3 and of the corresponding racemic alcohol.

FIGS. 3-5 illustrate chiral high performance liquid chromatography (HPLC) analyses of the alcohols obtained by allylation with allylation reagent 3 of benzaldehyde, cinnamaldehyde and dihydrocinnamaldehyde, respectively. In each of FIGS. 3-5, the chiral HPLC analysis of the corresponding racemic alcohol is also shown. FIGS. 6-10 show the $^{19}$F NMR ($C_6D_6$, 282 MHz) spectra of the Mosher esters of the alcohols obtained by allylation with allylation reagent 3 of isovaleraldehyde, cyclohexanecarboxaldehyde, pivaldehyde, benzyloxyacetaldehyde and tert-butyldimethylsilyloxyacetaldehyde, respectively. As shown in each of FIGS. 3-10, one optical isomer of the alcohol product is formed in excess of the other optical isomer, thereby showing that each reaction is enantioselective.

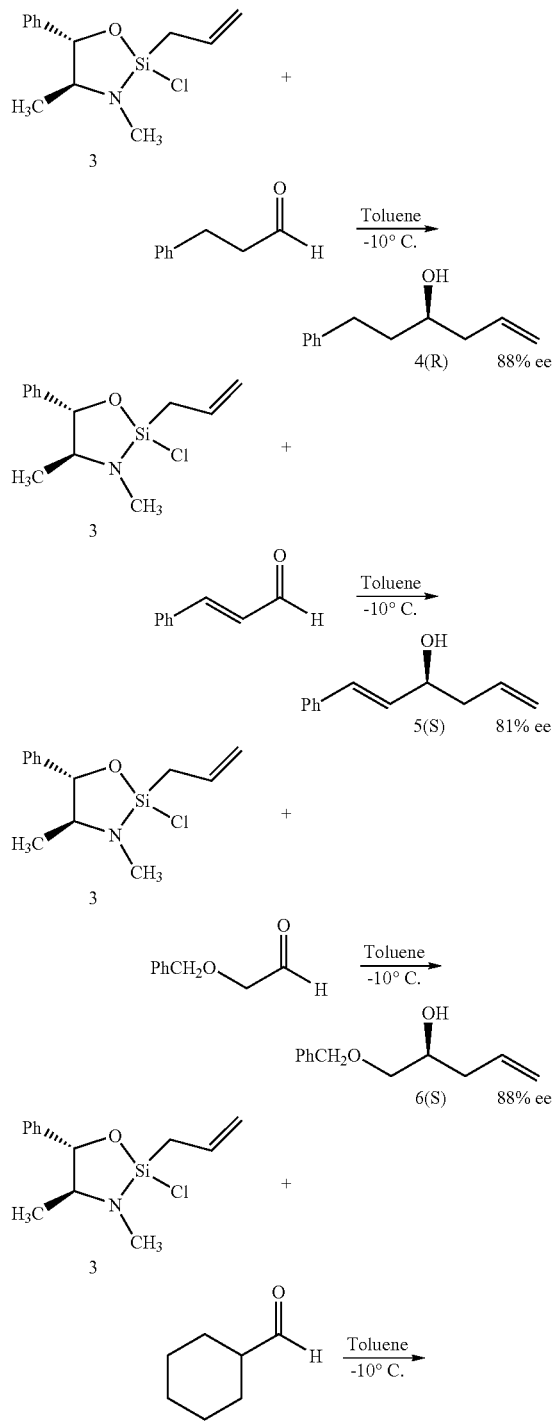

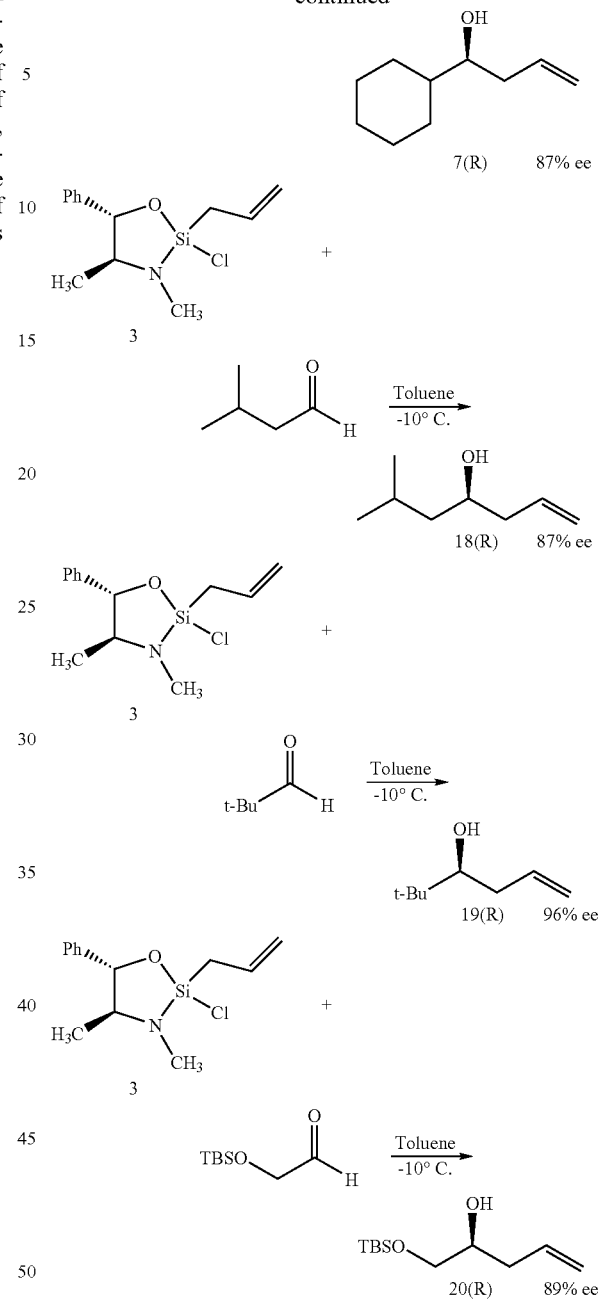

The aldehyde:reagent ratio may vary from about 1.5:1 to about 5:1, which is an exemplary range of ratios for the reaction of inexpensive aldehydes, or the aldehyde:reagent ratio may be about 1:1.5, which is an exemplary ratio for expensive aldehydes. In an exemplary embodiment of the invention, the asymmetric allylations shown in Schemes 2 and 3 may be performed using 1.5 equivalents of reagent 3 for every equivalent of the aldehyde.

Additional exemplary chiral allylation reagents include reagents 8 and 9, which may be formed in accordance with Scheme 4, and which react with benzaldehyde to give 1-phenyl-3-buten-1-ol with an enantioselectivity of 42% and 58%, respectively.

Scheme 4

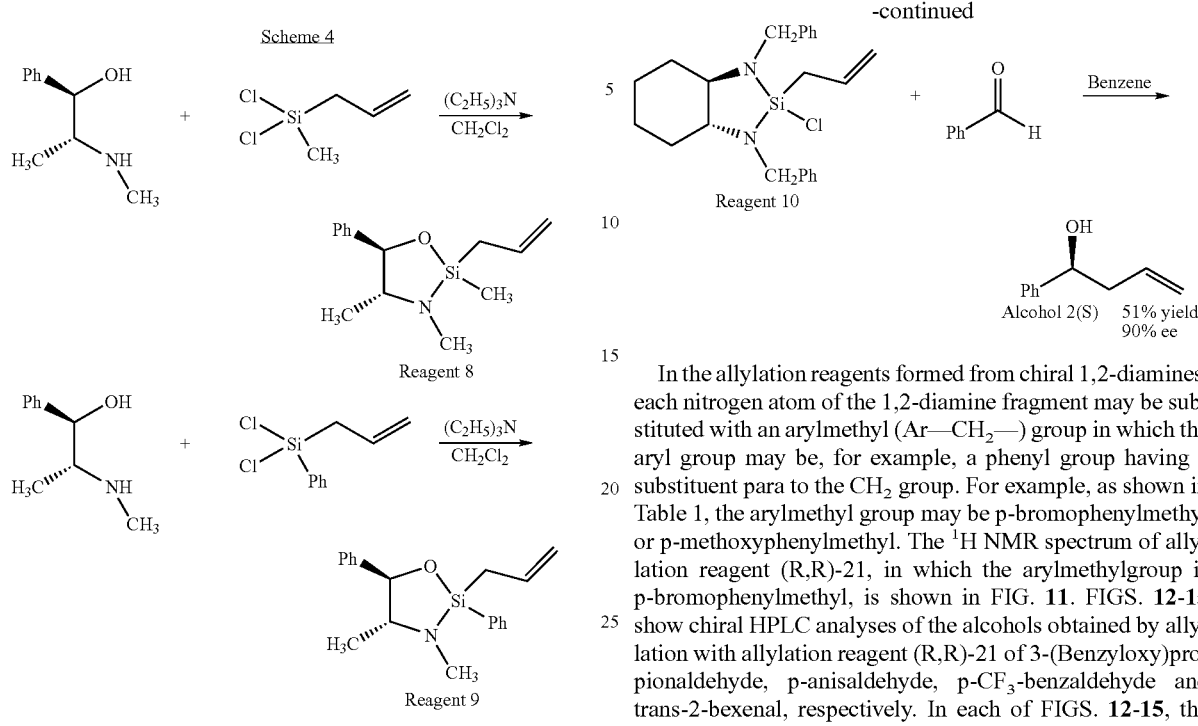

Figure 2:
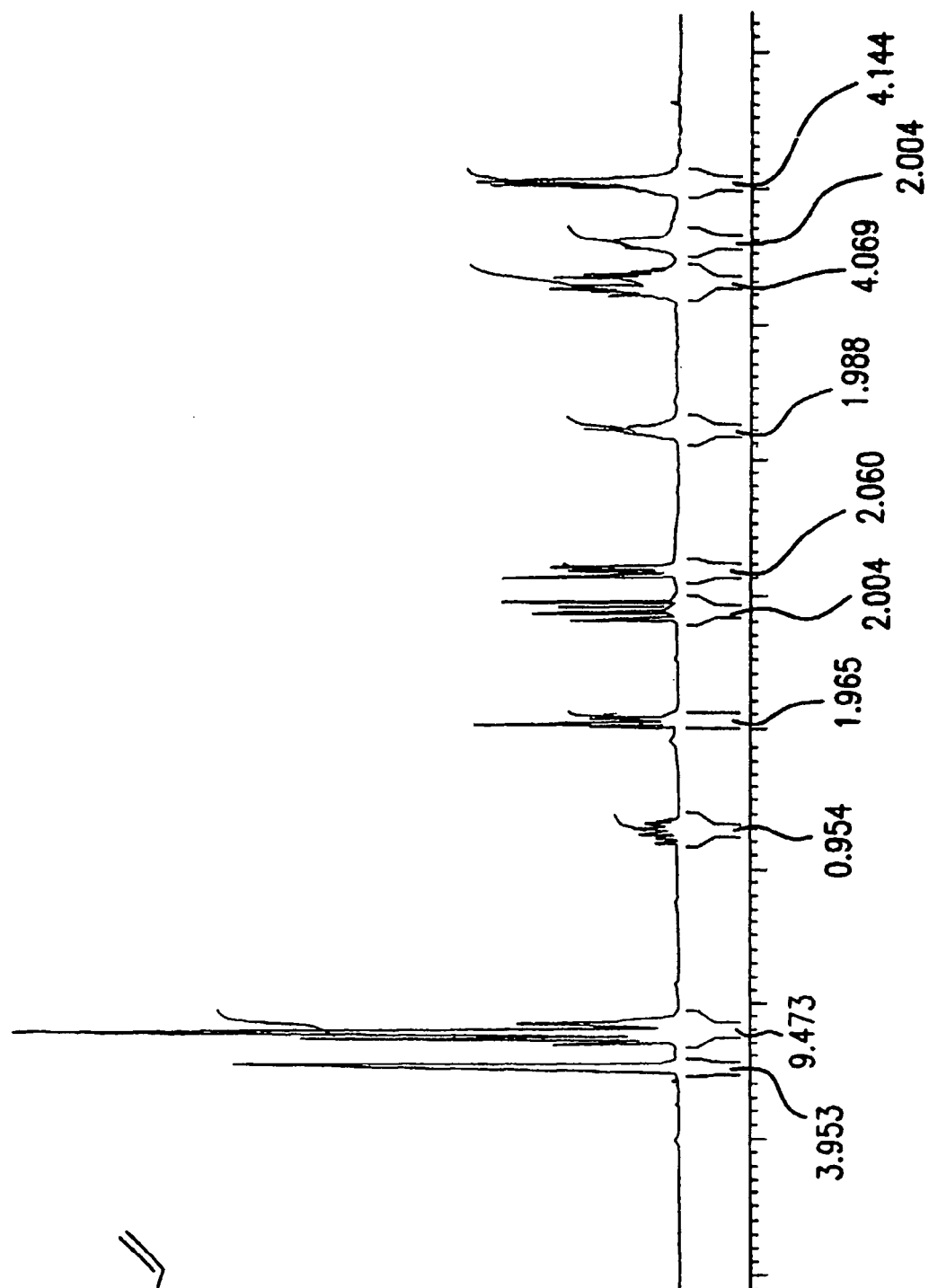
FIG. 2 shows the $^1$H NMR spectrum of allylation reagent 10.
Figure 2:
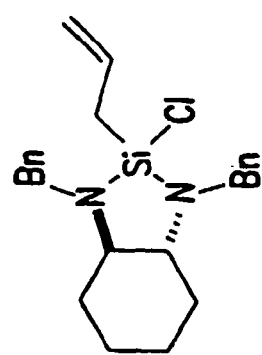

The allylation reagents of the invention may also be formed from diamines, including chiral 1,2-diamines. Exemplary chiral diamines include diamines having the formula (3) in which $X_2$ and $X_1$ are the same group NR, where R is methyl, benzyl, or phenyl; alternatively, $X_2$ and $X_1$ may be two different groups NR' and NR", where each of R' and R" is independently $C_{1-10}$ alkyl, $C_{6-10}$ aryl, or $C_{3-9}$ heteroaryl. For example, the reaction of (1R,2R)-N,N-Dibenzyl-cyclohexane-1,2-diamine with allyltrichlorosilane and DBU (diazabicycloundecene) in $CH_2Cl_2$ gave chiral allylation reagent 10, as shown in Scheme 5, with 99% crude yield and in sufficient purity for use in the allylation reaction. The $^1$H NMR spectrum of reagent 10, shown in FIG. 2, is in agreement with the structure of reagent 10. Reaction of reagent 10 with benzaldehyde in benzene for 72 hours led to the production of alcohol 2(S) in 51% yield and 90% ee. Accordingly, the reaction of reagent 10 with aromatic and conjugated aldehydes provides high enantioselectivity.

Scheme 5

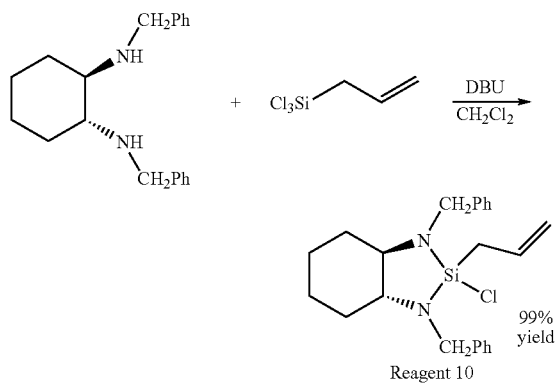

Figure 11:
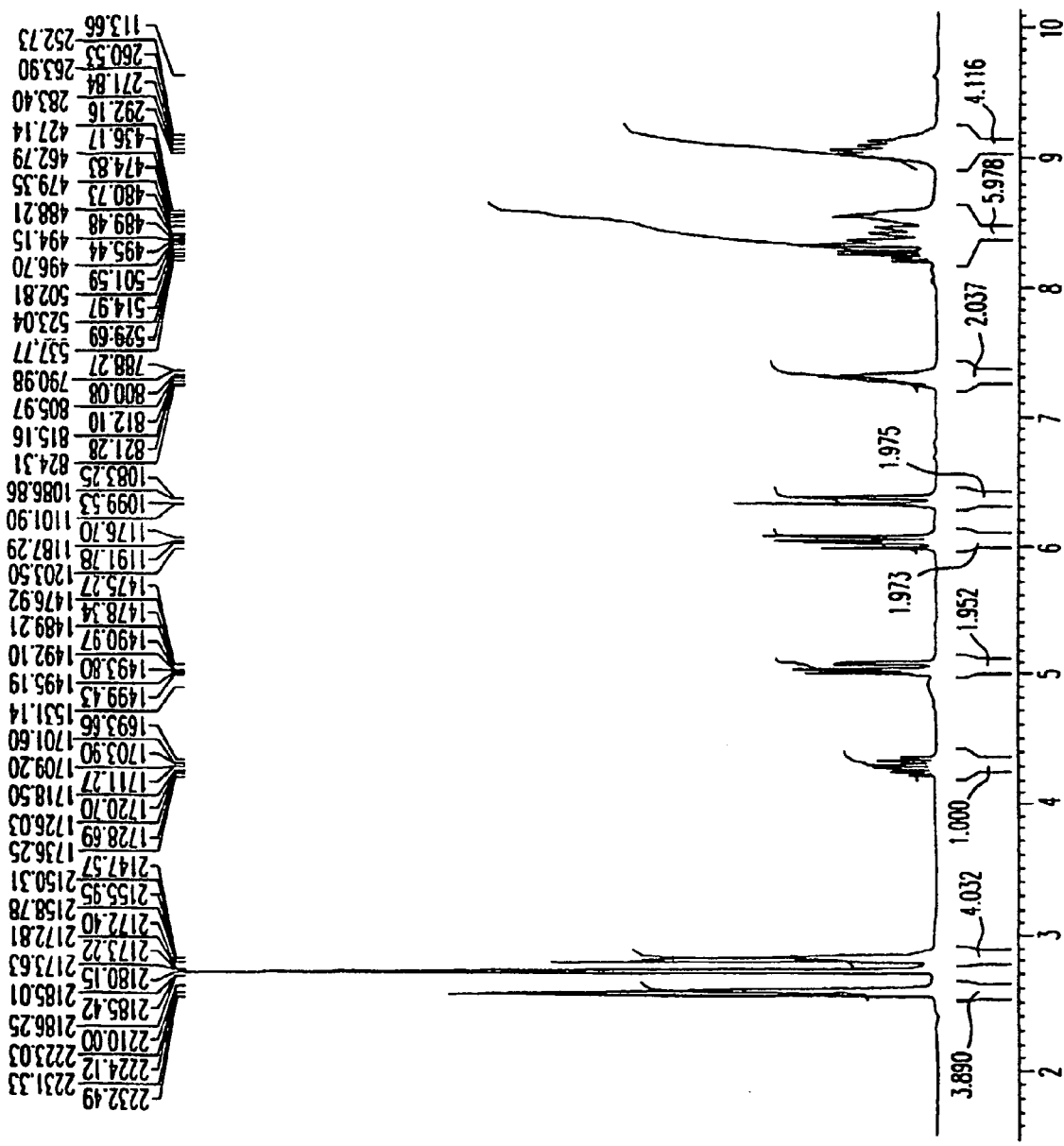
FIG. 11 shows the $^1$H NMR spectrum of allylation reagent (R,R)-21.

In the allylation reagents formed from chiral 1,2-diamines, each nitrogen atom of the 1,2-diamine fragment may be substituted with an arylmethyl (Ar—$CH_2$—) group in which the aryl group may be, for example, a phenyl group having a substituent para to the $CH_2$ group. For example, as shown in Table 1, the arylmethyl group may be p-bromophenylmethyl or p-methoxyphenylmethyl. The $^1$H NMR spectrum of allylation reagent (R,R)-21, in which the arylmethylgroup is p-bromophenylmethyl, is shown in FIG. 11. FIGS. 12-15 show chiral HPLC analyses of the alcohols obtained by allylation with allylation reagent (R,R)-21 of 3-(Benzyloxy)propionaldehyde, p-anisaldehyde, p-$CF_3$-benzaldehyde and trans-2-hexenal, respectively. In each of FIGS. 12-15, the chiral HPLC analysis of the corresponding racemic alcohol is also shown. Each of FIGS. 12-15 shows that one optical isomer of the alcohol product is formed in excess of the other optical isomer, thereby showing that each reaction is enantioselective.

The reaction of allylation reagent (R,R)-21 with the aldehydes shown in Tables 2 and 3, proceeds with high yield and enantioselectivity. Moreover, as shown in Scheme 6, Aldehyde 22 reacts with reagents (R,R)-21 and (S,S)-21 to give, respectively, syn β-benzyloxy alcohol 23 and anti β-benzyloxy alcohol 24.

TABLE 1

Optimization of the Diamine Auxiliary.

| entry[a] | X | R | yield(%)[b] | ee(%)[c] |
|---|---|---|---|---|
| | H | $PhCH_2CH_2$ | 79 | 96 |
| | H | Ph | 61 | 94 |
| | OMe | $PhCH_2CH_2$ | 77 | 98 |
| | Br | $PhCH_2CH_2$ | 90 | 98 |
| | Br | Ph | 69 | 98 |

[a]Reactions run with silane (1.0 equiv) and aldehyde (1.0 equiv) in $CH_2Cl_2$ at −10° C. for 20 h.
[b]Isolated yield.
[c]Determined by chiral HPLC analysis or by the Mosher ester method. See the supporting information.

TABLE 2

Enantioselective Allylation of Aliphatic Aldehydes.

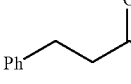

| entry[a] | aldehyde | product | yield(%)[b] | ee(%)[c] |
|---|---|---|---|---|
| |  | 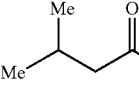 | 90 | 98 |
| |  | 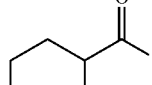 | 80[d] | 96 |
| |  | 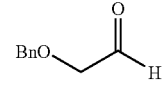 | 93 | 96 |
| |  | 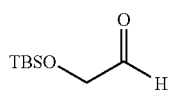 | 67 | 97 |
| |  | | 87 | 98 |
| | | | 61 | 98 |

[a]Reactions run with silane 3 (1.0 equiv) and aldehyde (1.0 equiv) in CH$_2$Cl$_2$ at −10° C. for 20 h.

[b]Isolated yield.

[c]Determined by chiral HPLC analysis or by the Mosher ester method. See the supporting information.

[d]Due to product volatility, an alternative workup and purification was employed. See the supporting information.

TABLE 3

| entry[a] | aldehyde | product | yield(%)[b] | ee(%)[c] |
|---|---|---|---|---|
| | Ph-CHO | Ph-CH(OH)-CH2-CH=CH2 | 69 | 98 |
| [d] | p-MeO—C6H4-CHO | p-MeO—C6H4-CH(OH)-CH2-CH=CH2 | 62 | 96 |
| | p-CF3—C6H4-CHO | p-CF3—C6H4-CH(OH)-CH2-CH=CH2 | 66 | 96 |
| [e] | Ph-CH=CH-CHO | Ph-CH=CH-CH(OH)-CH2-CH=CH2 | 66 | 96 |
| [e] | n-Pr-CH=CH-CHO | n-Pr-CH=CH-CH(OH)-CH2-CH=CH2 | 71[f] | 95 |

[a]Reactions: run with silane 3 (1.0 equiv) and aldehyde (1.0 equiv) in CH$_2$Cl$_2$ at −10° C. for 20 h.
[b]Isolated yield.
[c]Determined by chiral HPLC analysis or by the Mosher ester method. See the supporting information.
[d]Reaction run for 60 h.
[e]Reaction run at 8° C. for 72 h.
[f]Due to product volatility, an alternative workup and purification was employed. See the supporting information.

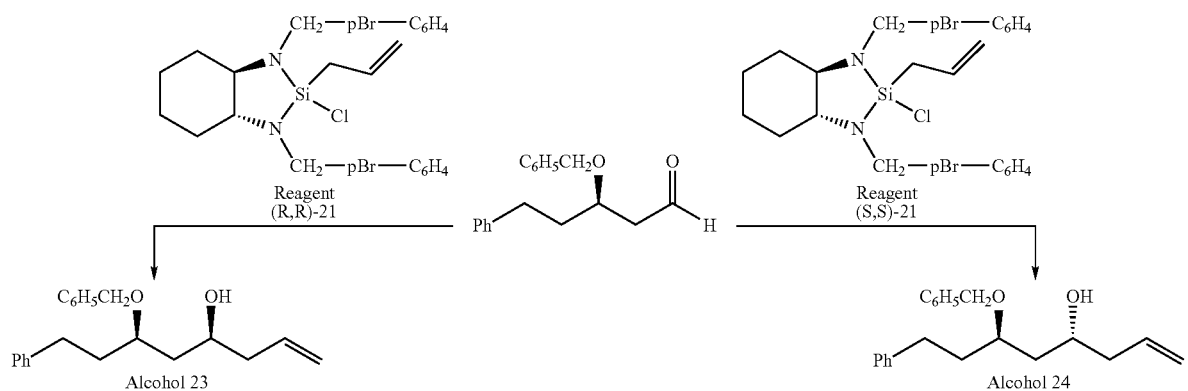

Scheme 6

In another embodiment of the invention, the reagent is an allylation reagent and has formula (11)

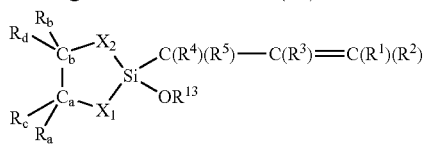
(11)

where $OR^{13}$ is an alkoxy group, and $R^{13}$ is $C_1$-$C_{10}$ alkyl, $C_{6-10}$ aryl, or $C_{3-9}$ heteroaryl. The reagent may be formed, for example, by the reaction of an alcohol $HOR^{13}$ with allylation reagent 3 in the presence of a base. The base may be an amine, such as, for example, triethylamine. Exemplary allylation reagents containing an alkoxy group include reagents where the alkoxy group $OR^{13}$ is methoxy, isopropoxy, or butoxy. For example, the reaction of allylation reagent 25, in which $OR^{13}$ is isopropoxy, with 3-phenylpropanal gives the homoallylic alcohol with 94% ee, as shown in Scheme 7:

Scheme 7

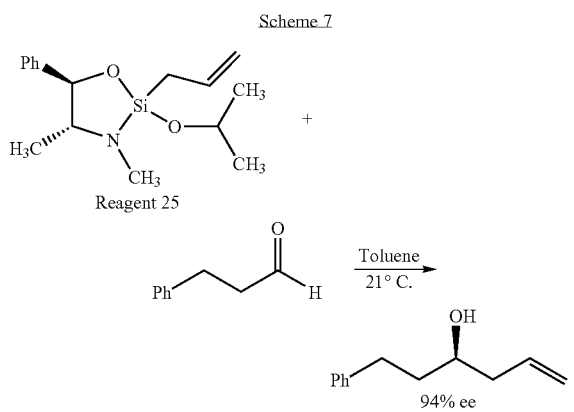

Reagent 25

94% ee

In another embodiment of the invention, a compound of formula

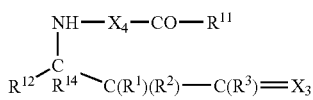
(9)

is formed by reacting a reagent of formula (4)

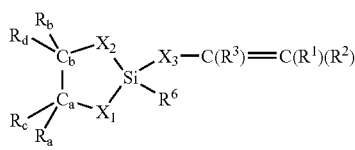

with a compound of formula $R^{12}C(R^{14})\!=\!\!N\!-\!\!X_4\!-\!\!CO\!-\!\!R^{11}$. In the compound of formula $R^{12}C(R^{14})\!=\!\!N\!-\!\!X_4\!-\!\!CO\!-\!\!R^{11}$, $R^{12}$ may be, for example, methyl, t-butyl, phenyl, 2-phenylethyl, (E)-2-phenylethenyl, benzyloxymethyl, cyclohexyl, iso-butyl, or tributylsilyloxymethyl. In the same compound, $R^{11}$ and $R^{14}$ may be, for example, hydrogen methyl, t-butyl, phenyl, 2-phenylethyl, (E)-2-phenylethenyl, benzyloxymethyl, cyclohexyl, iso-butyl, or tributylsilyloxymethyl.

The reagent may be an allylation reagent ($X_3\!=\!\!C(R^4)(R^5)$). For example, the reaction of the (S,S)-allylation reagent 26 with Ph-CH=N—NH—CO—CH$_3$ gives compound 27 in 98% ee and 80% yield, as shown in Scheme 8:

Scheme 8

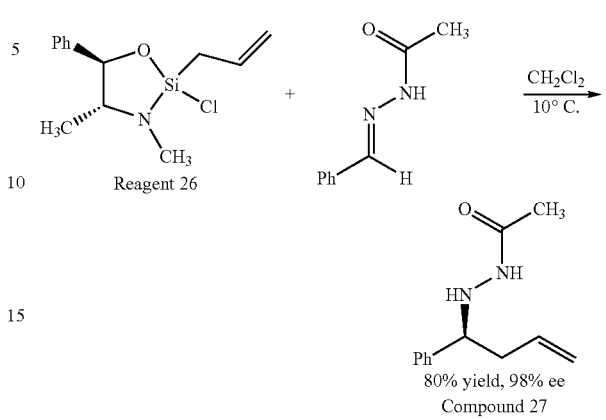

Reagent 26

80% yield, 98% ee
Compound 27

The reagent having the formula (4)

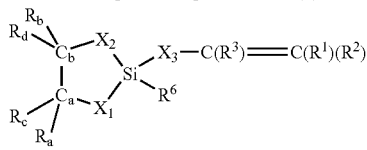

may be a reagent in which $X_3\!=\!\!O$. This reagent may be prepared by reacting a second reagent having formula

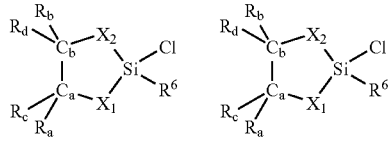

with one equivalent of a lithium enolate of the formula Li—O—C($R^3$)=C($R^1$)($R^2$). The second reagent may in turn be prepared by a compound having formula (3) with a silane having the formula $SiCl_3R^6$, which may be, for example, tetrachlorosilane.

The reagent having formula (5)

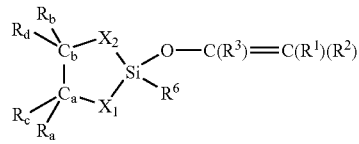

may react with an aldehyde $R^{10}$—CHO to form a compound having formula (21)

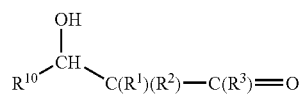

The reaction may be performed under similar conditions to those used for the reaction of $R^{10}$—CHO with an allylation reagent.

Similarly, the reagent having formula (5)

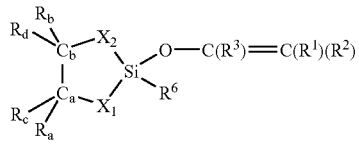
(5)

may react with a compound of the formula $R^{12}C(R^{14})=N-X_4-CO-R^{11}$ to form a compound having formula

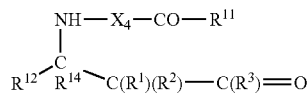
(22)

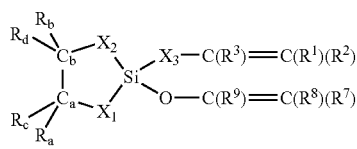

The reaction may be performed under similar conditions to those used for the reaction of a compound of the formula $R^{12}C(R^{14})=N-X_4-CO-R^{11}$ with an allylation reagent.

In another embodiment of the invention, a reagent having formula (18)

(18)

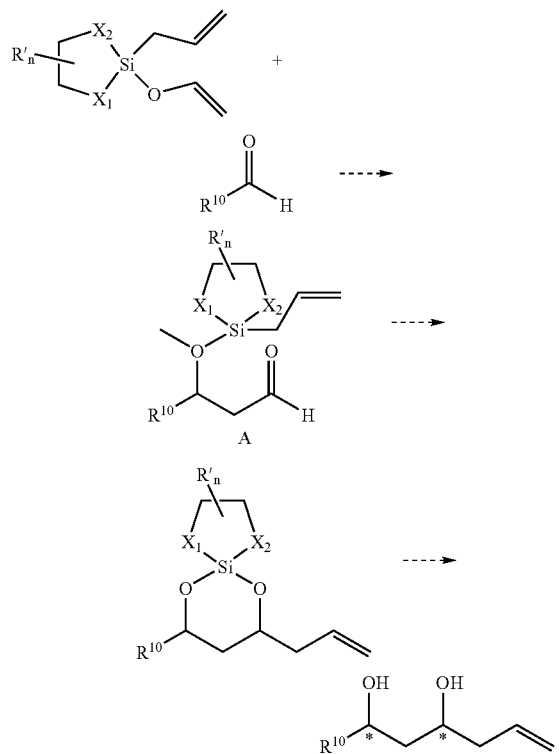

is reacted with an aldehyde to give a diol. Without wishing to be bound by any theory or mechanism, it is believed that the formation of the diol takes place according to Scheme 9, in which the enol terminal carbon attacks the aldehyde to form aldol addition intermediate A, which further undergoes a diastereoselective intramolecular allylation to give a diol having two chiral centers.

The reagent may be, for example, an allylation reagent containing an enol group and having formula

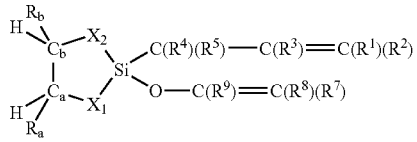

which may be formed by reacting $(R^7)(R^8)C=C(R^9)OLi$ with an allylation reagent of formula (12)

(12)

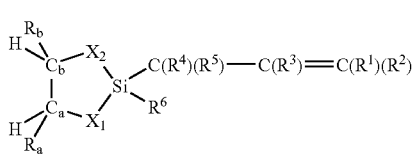

where $R^6$ is halogen or $-OSO_2CF_3$. As an example, the substituents $R^7$, $R^8$ and $R^9$ may each be independently hydrogen, methyl, or phenyl.

The allylation reagent containing an enol group may be formed by treating allylation reagent 1 with a lithium enolate, which may be generated, for example, by treatment of a vinyltrimethoxysilane of the formula $R^7R^8C=CR^9OSiMe_3$ with methyllithium in ether. For example, treatment of $H_2C=CHOSiMe_3$ with methyllithium in ether gives acetaldehyde lithium enolate, which reacts with reagent 1 to give allylenolsilane reagent 11 with 72% yield, as shown in Scheme 10. Reagent 11 may be distilled to purity, and has a shelf-life of at least several weeks without noticeable decomposition.

When treated with benzaldehyde in benzene at 50° C. for 8 hours, reagent 11 reacted to form diol 12 with 66% yield as an 8:1 syn:anti mixture of diastereomers. The direct allylation product 2 was also obtained with 13% yield. The reaction of 11 with cyclohexanecarboxaldehyde for 13 hours gave diol 13 with 56% yield as a 10:1 syn:anti mixture of diastereomers. The allylation product 7 was also obtained with 15% yield, as shown in Scheme 10. The allylation reagent may be reacted with the aldehyde $R^{10}CHO$ to give a diol in a solvent, which may be, for example, toluene, tetrahydrofuran, N,N-dimethylformamide, ethyl acetate, dichloromethane, hexane, t-butyl methyl ether, diethyl ether, acrylonitrile, or benzene. In an exemplary embodiment, the concentration of the aldehyde in the solvent may range from 0.05 M to 0.5 M. For example, a concentration of about 0.2 M aldehyde may be used. In another exemplary embodiment, the reaction may be performed in the absence of solvent. Exemplary aldehydes include aldehydes where Rio is methyl, t-butyl, phenyl, 2-phenylethyl, (E)-2-phenylethenyl, benzyloxymethyl, cyclohexyl, iso-butyl, or tributylsilyloxymethyl.

Scheme 10

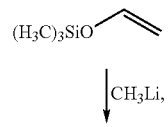

$\downarrow$ CH₃Li, diethyl ether, 0° C.

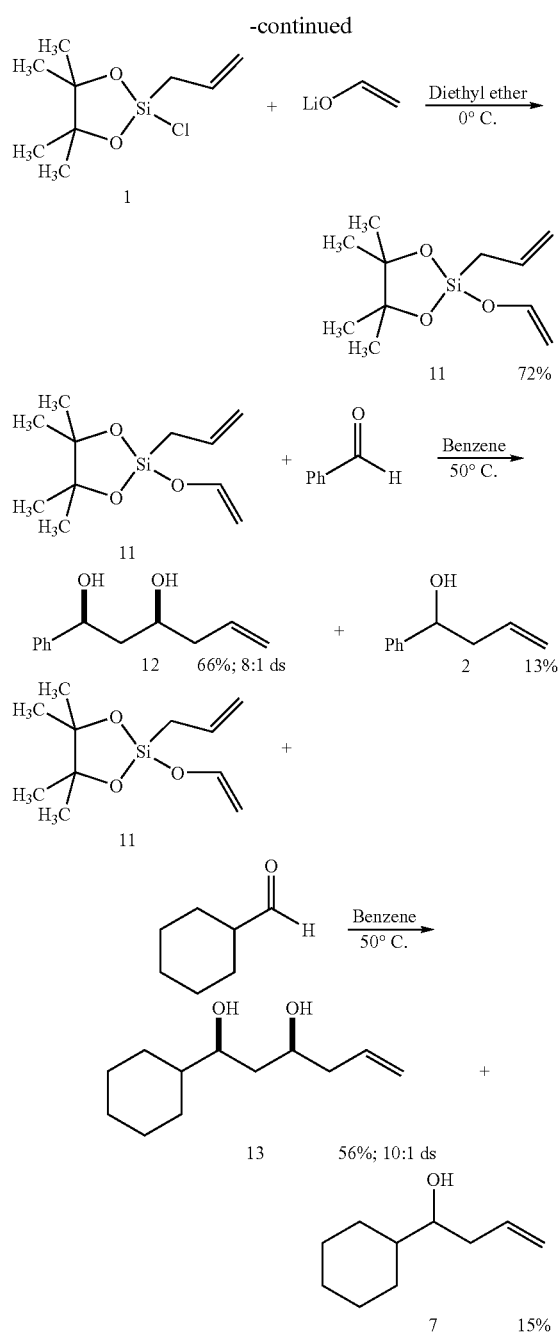

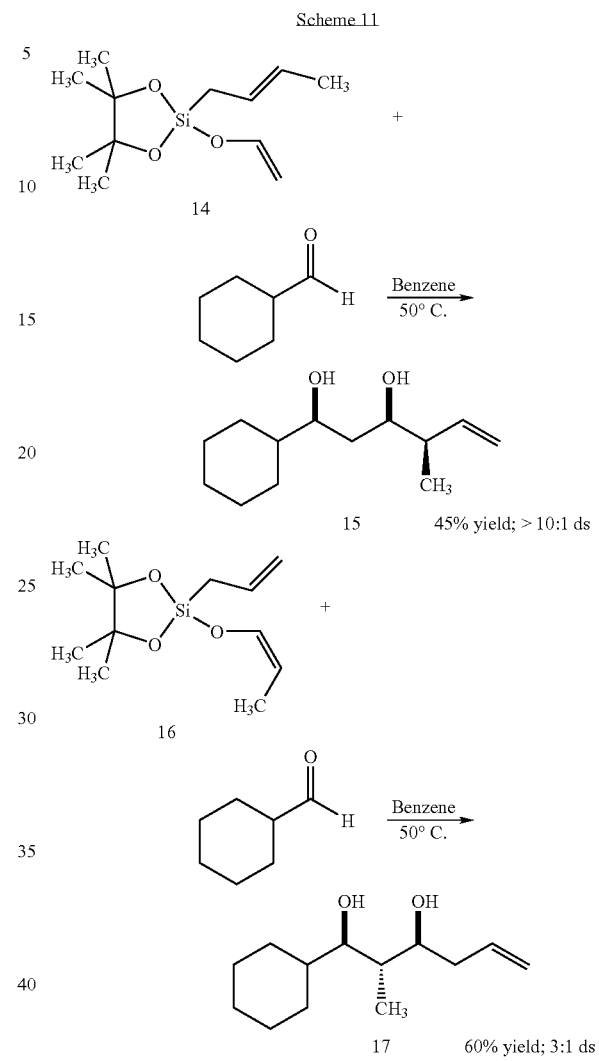

10:3:1 mixture of diastereomers with 60% yield. Diol 17 was shown to be the major diastereomer.

As another example, trans-crotylenolsilane 14 reacted with cyclohexanecarboxaldehyde according to the equation shown in Scheme 11 to form diol 15, in which 3 new chiral centers are created, in 45% yield and >10:1 diastereoselectivity. No crotylation product analogous to 7 was obtained (see Scheme 10). Without wishing to be bound by any mechanism or theory, it is believed that the trans-disposed methyl group of 14 slows the rate of transfer of the crotyl group, and that therefore no crotyl group transfer occurs until after the formation of an aldol addition intermediate, in accordance with Scheme 9.

As another example, shown in Scheme 11, allyl-cis-enolsilane 16 reacted with cyclohexanecarboxaldehyde to give a An allylation reagent containing an enol group may also be formed, for example, by treating allylation reagent 29, formed from the reaction of chiral diol 28 with allyltrichlorosilane as previously discussed, in connection with equation (I), with a lithium enolate. For example, allylation reagent 30 may be formed as shown in Scheme 12. When allylation reagent 30 is reacted with benzaldehyde, the corresponding diol is formed in 70% yield and 68% ee.

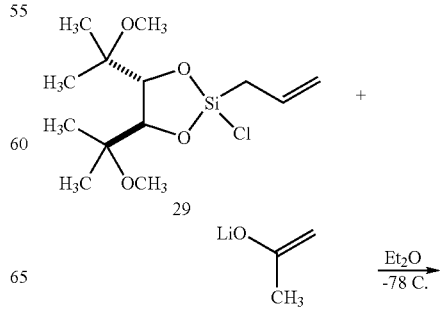

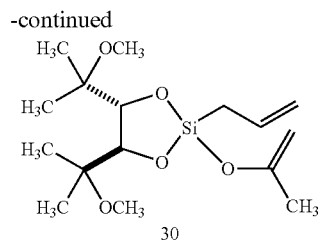
30

The reagent which reacts with an aldehyde to give a diol may be a reagent containing two enol groups and having formula (15)

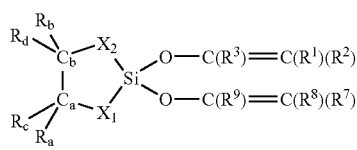
(15)

In one embodiment of the invention, the group $C(R^9)=C(R^8)(R^7)$ is identical to the group $C(R^3)=C(R^1)(R^2)$. In this embodiment, the reagent may be formed by reacting a second reagent of the formula (6)

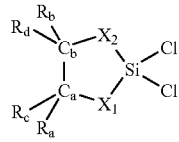

with two equivalents of a lithium enolate of the formula Li—)—$C(R^3)=C(R^1)(R^2)$, or by reacting a third reagent of formula (5)

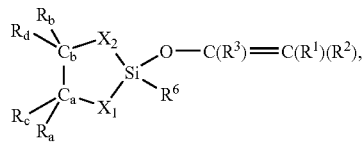

where $R^6$ is a halogen or —$OSO_2CF_3$, with one equivalent of a lithium enolate of formula Li—O—$C(R^3)=C(R^1)(R^2)$. The reagent containing two enol groups may react with an aldehyde $R^{10}$—CHO to form a diol under similar conditions to those used for the reaction of $R^{10}$—CHO with an allylation reagent containing an enol group.

In another embodiment, a compound of formula (19)

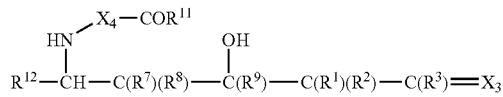

is formed by reacting a reagent of formula (20)

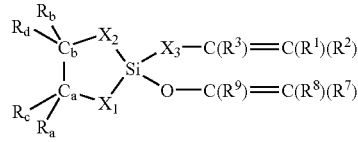

with a compound of the formula $R^{12}C(R^{14})=N-X_4-CO-R^{11}$ to form the compound of formula (19).

The reagent of formula (20)

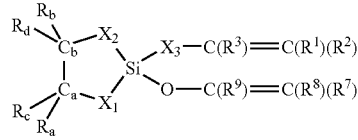

may be an allylation reagent containing an enol group ($X_3=C(R^4)(R^5)$) or a reagent containing two enol groups ($X_3=O$). In an exemplary embodiment where $X_3=O$, the two enol groups O—$C(R^9)=C(R^8)(R^7)$ and O—$C(R^3)=C(R^1)(R^2)$ are identical. The reagent may be reacted with the compound of the formula $R^{12}C(R^{14})=N-X_4-CO-R^{11}$ in a solvent such as toluene, tetrahydrofuran, N,N-dimethylformamide, ethyl acetate, dichloromethane, hexane, t-butyl methyl ether, diethyl ether, acrylonitrile, or benzene. In an exemplary embodiment, the concentration of the compound of the formula $R^{12}C(R^4)=N-X_4-CO-R^{11}$ in the solvent may range from 0.05 M to 0.5 M. For example, a concentration of about 0.2 M of compound of the formula $R^{12}C(R^{14})=N-X_4-CO-R^{11}$ may be used. In another exemplary embodiment, the reaction may be performed in the absence of solvent. Examples of the compound of the formula $R^{12}C(R^{14})=N-X_4-CO-R^{11}$ include compounds where $R^{12}$ is methyl, t-butyl, phenyl, 2-phenylethyl, (E)-2-phenylethenyl, benzyloxymethyl, cyclohexyl, iso-butyl, or tributylsilyloxymethyl, and each of $R^{11}$ and $R^{14}$ is independently hydrogen, methyl, t-butyl, phenyl, 2-phenylethyl, (E)-2-phenylethenyl, benzyloxymethyl, cyclohexyl, iso-butyl, or tributylsilyloxymethyl.

The invention may be further described by the following examples, which are illustrative of the invention but which are not intended to define the scope of the invention in any way.

EXAMPLES (eq. II)

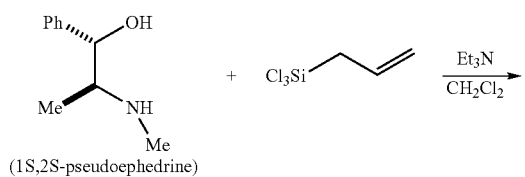

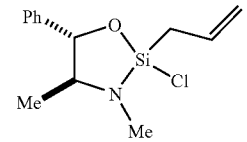

Preparation of (4S,5S)-2-Allyl-2-chloro-3,4-dimethyl-5-phenyl-[1,3,2]oxazasilolidine: To a cooled (0° C.) solution of allyltrichlorosilane (101 mL, 0.696 mol) in methylene chloride (1.8 L) under argon was added triethylamine (170 mL, 1.21 mol). (1S,2S)-pseudoephedrine (100 g, 0.605 mol) was then added portionwise over 30 min, to maintain internal temperature below 15° C. After the addition was complete the mixture was stirred for 12 hours at ambient temperature. The methylene chloride was removed by distillation and the residue was diluted with pentane (1.5 L). The mixture was vigorously stirred for 12 hours to ensure complete precipitation of the triethylamine salts. Filtration of the resulting suspension through a pad of celite and concentration of the filtrate by distillation afforded the crude product as a pale yellow oil. Purification by distillation under reduced pressure (bp~120 C, 5 mm Hg) provided 149 g (92%) of (4S, 5S)-2-Allyl-2-chloro-3,4-dimethyl-5-phenyl-[1,3,2]oxazasilolidine as a ~2:1 mixture of diastereomers.

was added triethylamine (1.2 mL, 8.6 mmol). 2-Propanol (0.6 mL, 7.8 mmol) was added slowly by syringe and the mixture was allowed to stir for 12 hours. The methylene chloride was removed by distillation and pentane (20 ml) was added to the residue. The mixture was stirred for 3 hours. The mixture was then filtered through a pad of celite. The filtrate was concentrated to afford an oil which was distilled under reduced pressure (b.p. ~72° C., ~0.2 mm Hg) to yield 1.08 g (48%) of (4S,5S)-2-Allyl-2-isopropoxy-3,4-dimethyl-5-phenyl-[1,3,2]oxazasilolidine as a ~2:1 mixture of diastereomers.

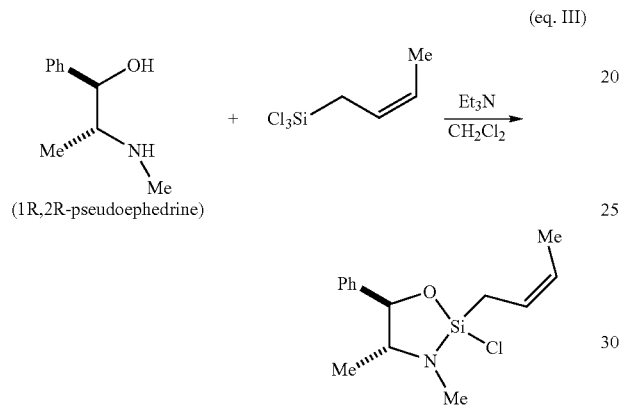

(eq. III)

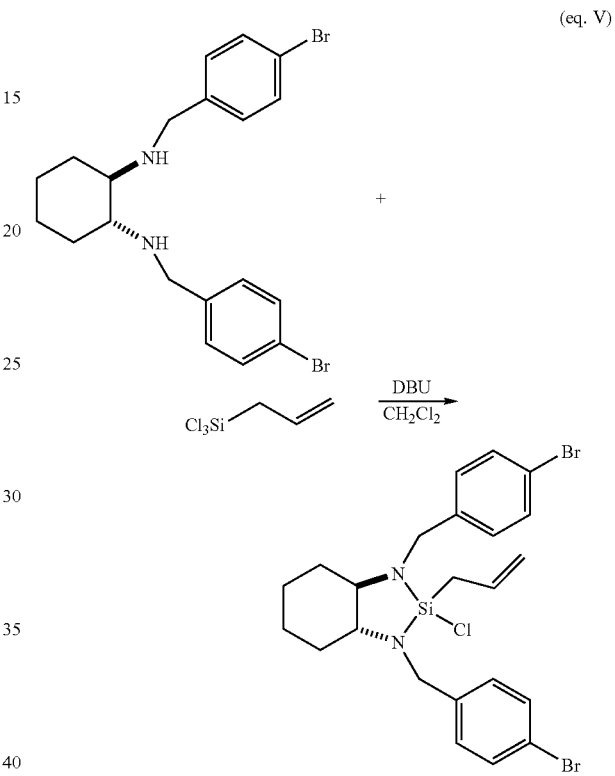

(eq. V)

Preparation of (4R,5R)-2-(cis)-but-2-enyl-2-chloro-3,4-dimethyl-5-phenyl-[1,3,2]oxazasilolidine: To a cooled (0° C.) solution of cis-but-2-enyl-trichlorosilane (7.0 g, 37 mmol) in methylene chloride (80 mL) was added triethylamine (8.75 mL, 63 mmol). (1R,2R)-psuedoephedrine (5.20 g, 31 mmol) was added portionwise and the mixture was allowed to stir for 12 hours. The methylene chloride was removed by distillation and pentane (50 mL) was added to the residue. The mixture was allowed to stir for 1 hour to ensure complete precipitation of the triethylamine salts. The suspension was filtered through a pad of celite. The filtrate was concentrated to give a pale yellow oil which was distilled under reduced pressure to give 5.85 g (68%) of (4R,5R)-2-(cis)-but-2-enyl-2-chloro-3,4-dimethyl-5-phenyl-[1,3,2]oxazasilolidine as a ~2.4:1 mixture of diastereomers.

Preparation of (4R,5R)-2-Allyl-1,3-bis-(4-bromo-benzyl)-2-chloro-octahydro-benzo[1,3,2]diazasilole: To a cooled (0° C.) solution of allyltrichlorosilane (2.05 ml, 14.1 mmol) and 1,8-diazabicyclo[5.4.0]undec-7-ene (4.24 ml, 28.4 mmol) in dichloromethane (50 ml) was added (R,R)-N,N'-bis-(4-bromo-benzyl)-cyclohexane-1,2-diamine (5.37 g, 11.9 mmol) in dichloromethane (20 ml) over 50 min. After 2 h, the mixture was warmed to room temperature, and was stirred for 13 h. The reaction mixture was concentrated. Diethylether (60 ml) was added, and the mixture was stirred for 1 h. The mixture was filtrated through a pad of celite with ether washes (2×10 ml). The filtrate was concentrated. Benzene (10 ml) was added, and the solution was concentrated. This procedure was repeated and upon standing in a freezer, the resulting oil solidified to give 5.37 g (88%) of (4R ,5R)-2-Allyl-1,3-bis-(4-bromo-benzyl)-2-chloro-octahydro-benzo[1,3,2]diazasilole as a white solid.

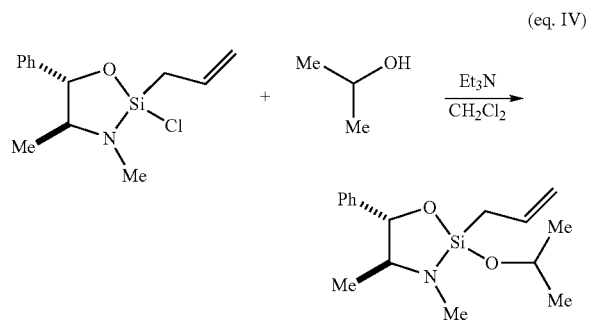

(eq. IV)

Preparation of (4S,5S)-2-Allyl-2-isopropoxy-3,4-dimethyl-5-phenyl-[1,3,2]oxazasilolidine: To a solution of (4S, 5S)-2-Allyl-2-chloro-3,4-dimethyl-5-phenyl-[1,3,2]oxazasilolidine (2.08 g, 7.8 mmol) in methylene chloride (25 mL)

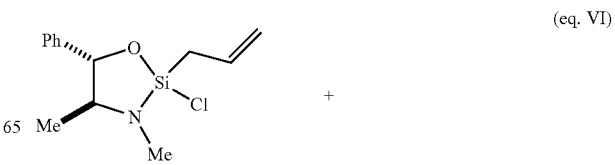

(eq. VI)

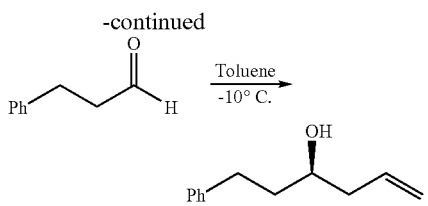

Enantioselective allylation of dihydrocinnamaldehyde to give (3R)-1-phenyl-hex-5-en-3-ol: To a cooled (−10° C.) solution of (4S,5S)-2-Allyl-2-chloro-3,4-dimethyl-5-phenyl-[1,3,2]oxazasilolidine (380 mg, 1.5 mmol) in toluene (5 mL) was added dihydrocinnamaldehyde (1.0 mmol). The reaction mixture was maintained at −10° C. for 2 h. To this cooled solution was added 1N HCl (4 mL) and EtOAc (4 mL) and the mixture was vigorously stirred for 15 min. The layers were separated and the aqueous layer was extracted with EtOAc (2×5 mL). The combined organics were dried (MgSO$_4$), filtered, and concentrated. The residue was purified by flash chromatography on silica gel to give (3R)-1-phenyl-hex-5-en-3-ol in 84% yield and 88% enantiomeric excess (ee).

(eq. VII)

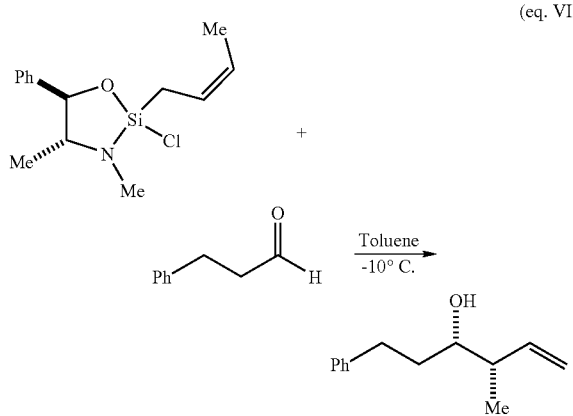

Enantioselective crotylation of dihydrocinnamaldehyde to give (3S,4S)-4-Methyl-1-phenyl-hex-5-en-3-ol: To a cooled (−10° C.) solution of (4R,5R)-2-((cis)-but-2-enyl)-2-chloro-3,4-dimethyl-5-phenyl-[1,3,2]oxazasilolidine (0.431 g, 1.5 mmol) in toluene (2.5 mL) was added dihydrocinnamaldehyde (0.132 mL, 1.0 mmol). The reaction mixture was allowed to stir for 12 hours at −10° C. To this solution was added 1N HCl (4 mL) and EtOAc (4 mL) and the mixture was stirred for 10 min. The layers were separated and the aqueous layer was extracted with EtOAc (3×5 mL). The combined organics were dried over MgSO$_4$, filtered, and concentrated. HPLC analysis of the residue at this stage revealed a syn:anti diastereoselectivity of 10:1, and an enantiomeric excess for the major syn product of 81%. The residue was purified by chromatography on silica gel to afford 0.116 g (61%) of (3S,4S)-4-Methyl-1-phenyl-hex-5-en-3-ol (81% ee).

(eq. VIII)

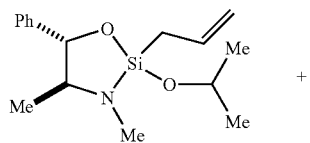

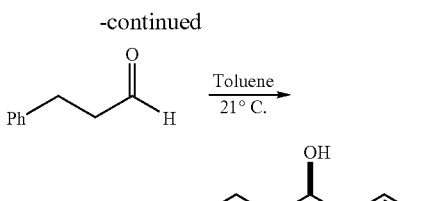

Enantioselective allylation of dihydrocinnamaldehyde to give (3R)-1-phenyl-hex-5-en-3-ol: To a solution of (4S,5S)-2-Allyl-2-isopropoxy-3,4-dimethyl-5-phenyl-[1,3,2]oxazasilolidine (0.437 g, 1.5 mmol) in toluene (2.5 mL) was added dihydrocinnamaldehyde (0.132 mL, 1.0 mmol). The mixture was allowed to stir at ambient temperature (~21° C.) for 18 hours. To this solution was added 1N HCl (4 mL) and EtOAc (4 mL) and the mixture was stirred for 10 min. The layers were separated and the aqueous layer was extracted with EtOAc (3×5 mL). The combined organics were dried over MgSO$_4$, filtered, and concentrated. The residue was purified by chromatography on silica gel (5% EtOAc/hexanes) to afford 0.119 g (69%) of (3R)-1-phenyl-hex-5-en-3-ol in 94% enantiomeric excess (ee).

(eq. IX)

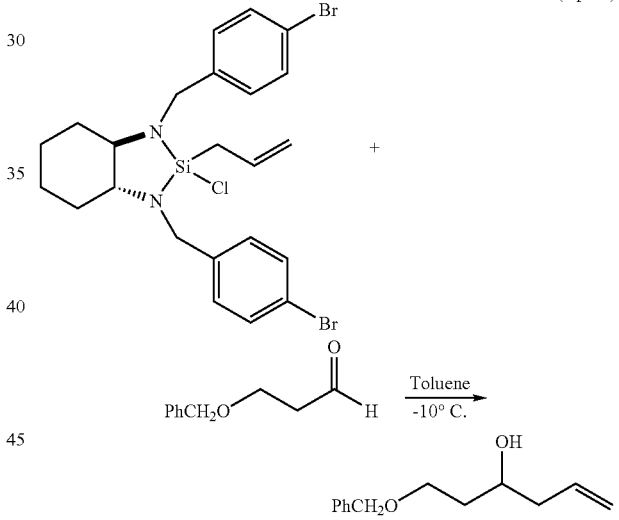

Enantioselective allylation of 3-benzyloxypropionaldehyde to give (3S)-1-benzyloxy-hex-5-en-3-ol: To a cooled (−10° C.) solution of (4R,5R)-2-Allyl-1,3-bis-(4-bromo-benzyl)-2-chloro-octahydro-benzo[1,3,2]diazasilole (1.0 mmol) in CH$_2$Cl$_2$ (5 mL) was added 3-benzyloxypropionaldehyde (1.0 mmol). The reaction mixture was transferred to a freezer (−10° C.) and maintained at that temperature for 20 h. To this cooled solution was added 1N HCl and EtOAc, and the mixture was vigorously stirred at room temperature for 15 min. The layers were separated and the aqueous layer was extracted with EtOAc 3 times. The combined organic layers were diluted with hexane, dried (MgSO$_4$), filtered, and concentrated. Purification of the residue by chromatography on silica gel gave (3S)-1-benzyloxy-hex-5-en-3-ol in 87% yield and 98% ee.

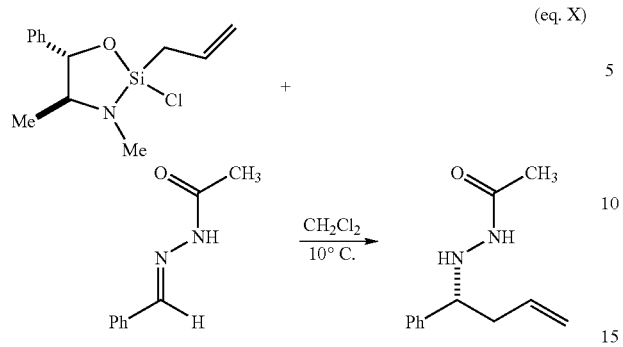

(eq. X)

Enantioselective allylation of acetic acid benzylidene-hydrazide (8) to give (1R)-acetic acid N'-(1-phenyl-but-3-enyl)-hydrazide: To a cooled (10° C.) solution of (4S,5S)-2-Allyl-2-chloro-3,4-dimethyl-5-phenyl-[1,3,2]oxazasilolidine (9.90 g, 37.0 mmol) in CH$_2$Cl$_2$ (300 mL) was added acetic acid benzylidene-hydrazide (5.00 g, 30.8 mol) as a solid. The resulting solution was stirred for 16 hours and methanol (40 mL) was then added. After 15 min all volatiles were removed by distillation and the residue was diluted with EtOAc (150 mL) and H$_2$O (500 mL). The phases were separated and the aqueous layer was extracted with EtOAc (2×150 mL). The combined organic layers were washed with H$_2$0 and brine, dried (MgSO$_4$), filtered and concentrated. Analysis of the residue by HPLC revealed an ee of 87%. The residue was dissolved in boiling toluene (80 mL) and the solution was then cooled to ambient temperature. Pentane (380 mL) was layered on top of the toluene solution and the resulting biphasic solution was allowed to stand for 16 hours. The resulting crystalline solid precipitate was filtered, washed (pentane: toluene (5:1)) and then dried in vacuo to give 5.04 g (80%) of (1R)-acetic acid N'-(1-phenyl-but-3-enyl)-hydrazide in 98% ee.

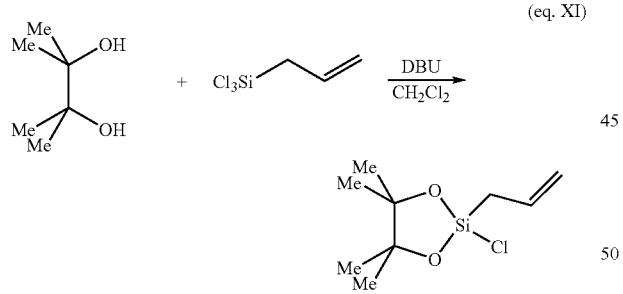

(eq. XI)

Preparation of 2-allyl-2-chloro-4,4,5 5-tetramethyl-[1,3,2] dioxasilolane: To a cooled (0° C.) solution of allyltrichlorosilane (4.9 mL; 34 mmol) in CH$_2$Cl$_2$ (50 mL) was added 1,8-Diazabicyclo[5.4.0]undec-7-ene (13 mL; 84 mmol). A solution of pinacol (4.0 g; 34 mmol) in CH$_2$Cl$_2$ (50 mL) was then added slowly and the resultant solution was warmed to room temperature and stirred for 12 hours. The solution was concentrated and the residue was treated with diethylether (100 mL). The mixture was stirred for 1 hour during which time the formation of a precipitate was observed. The mixture was then filtered and the filtrate was concentrated. The residue was distilled under reduced pressure to give 5.2 g (72%) of 2-allyl-2-chloro-4,4,5,5-tetramethyl-[1,3,2]dioxasilolane as a clear, colorless liquid.

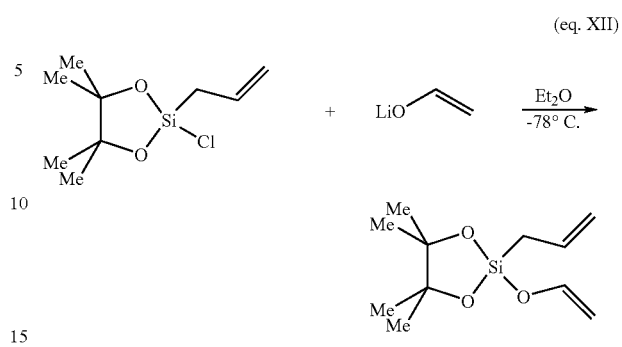

(eq. XII)

Preparation of 2-allyl-4,4,5,5-tetramethyl-2-vinyloxy-[1,3,2]dioxasilolane: To a cooled (0° C.) solution of MeLi (16.2 mL; 23 mmol; 1.4 M in Et$_2$0) was added trimethylvinyloxysilane (2.7 g; 23 mmol). The solution was warmed to room temperature and was stirred for 1 hour. The solution was cooled to −78° C., and 2-allyl-2-chloro-4,4,5,5-tetramethyl-[1,3,2]dioxasilolane (5.5 g; 25 mmol) was added. The solution was warmed to room temperature and stirred for 2 hours. The solution was diluted with pentane (20 mL), and the mixture was then filtered through a pad of celite. The filtrate was concentrated, and the residue was distilled under reduced pressure to give 3.8 g (70%) of 2-allyl-4,4,5,5-tetramethyl-2-vinyloxy-[1,3,2]dioxasilolane as a clear, colorless liquid.

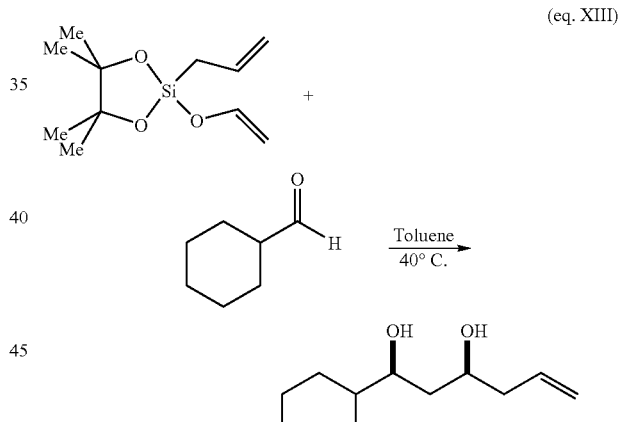

(eq. XIII)

Tandem aldol-allylation reaction of cyclohexanecarboxaldehyde to give (syn)-1-cyclohexyl-hex-5-ene-1,3-diol: To a solution of 2-allyl-4,4,5,5-tetramethyl-2-vinyloxy-[1,3,2]dioxasilolane (0.63 mmol) in toluene (0.4 mL) was added cyclohexanecarboxaldehyde (48 mg; 0.42 mmol). The solution was heated to 40° C. and stirred at that temperature for 24 h. The solution was cooled and 1 M HCl (5 mL) was added followed by ethyl acetate (5 mL). The mixture was stirred for 20 min and the layers were separated. The organic layer was washed with saturated aqueous NaHCO$_3$ (5 mL), washed with brine (5 mL), dried (Na$_2$SO$_4$), filtered, and concentrated. The residue was purified by chromatography on silica gel to give racemic (syn)-1-cycloliexyl-hex-5-ene-1,3-diol in 59% yield.

(eq. XIV)

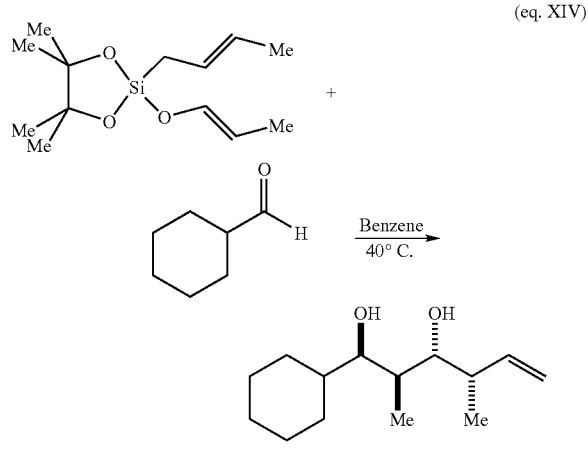

Tandem aldol-allylation reaction of cyclohexanecarboxaldehyde to give (syn,anti,syn)-1-cyclohexyl-2,4-dimethyl-hex-5-ene-1,3-diol: To a solution of (trans,trans)-2-but-2-enyl-4,4,5,5-tetramethyl-2-propenyloxy-[1,3,2] dioxasilolane (prepared by an exactly analogous procedure to that used for the preparation of 2-allyl-4,4,5,5-tetramethyl-2-vinyloxy-[1,3,2]dioxasilolane) (0.63 mmol) in benzene (0.4 mL) was added cyclohexanecarboxaldehyde (48 mg; 0.42 mmol). The solution was heated to 40° C. and stirred at that temperature for 132 h. The solution was cooled and 1 M HCl (5 mL) was added followed by ethyl acetate (5 mL). The mixture was stirred for 20 min and the layers were separated. The organic layer was washed with saturated aqueous NaHCO$_3$ (5 mL), washed with brine (5 mL), dried (Na$_2$SO$_4$), filtered, and concentrated. $^1$H NMR analysis at this stage revealed the presence of 4 diastereomeric products in a 86:11:3:1 ratio. The major product was isolated by chromatography on silica gel to give racemic (syn,anti,syn)-1-cyclohexyl-2,4-dimethyl-hex-5-ene-1,3-diol in 60% yield.

(eq. XV)

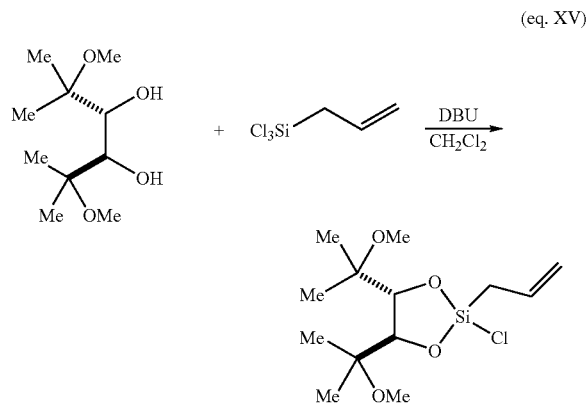

Preparation of (4R,5R)-2-allyl-2-chloro-4,5-bis-(1-methoxy-1-methyl-[1,3,2]dioxasilolane: To a cooled (0° C.) solution of allyltrichlorosilane (7.0 mL; 48 mmol) in CH$_2$Cl$_2$ (80 mL) was added 1,8-diazabicyclo[5.4.0]undec-7-ene (15 mL; 102 mmol). A solution of (3R,4R)-2,5-dimethoxy-2,5-dimethyl-hexane-3,4-diol (10.0 g; 48 mmol) in CH$_2$Cl$_2$ (80 mL) was then added and the mixture was allowed to warm to ambient temperature and stirred for 12 hours. The solution was concentrated and the residue was treated with diethyl-ether (100 mL). The mixture was stirred for 1 hour. The mixture was then filtered and the filtrate was concentrated. The residue was distilled under reduced pressure to give 6.6 g (44%) of (4R,5R)-2-allyl-2-chloro-4,5-bis-(1-methoxy-1-methyl-ethyl)-[1,3,2]dioxasilolane as a clear, colorless liquid.

(eq. XVI)

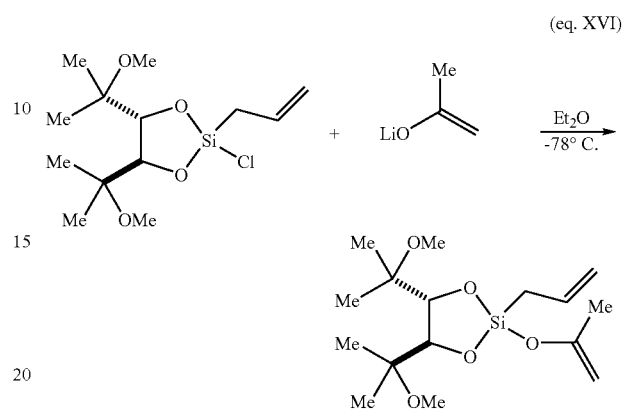

Preparation of (4R,5R)-2-allyl-2-isopropenyloxy-4,5-bis-(1-methoxy-1-methyl-ethyl)-[1,3,2]dioxasilolane: To a cooled (0° C.) solution of MeLi (13.0 mL; 21 mmol; 1.6 M in Et$_2$O) was added 2-(trimethylsilyloxy)propene (2.8 g; 21 mmol). The solution was stirred 30 minutes at 0° C., and then warmed to room temperature and was stirred for 1 hour. The mixture was recooled to 0° C., and (4R,5R)-2-allyl-2-chloro-4,5-bis-(1-methoxy-1-methyl-ethyl)-[1,3,2]dioxasilolane (6.6 g; 21 mmol) was added. The mixture was warmed to room temperature and stirred for 2 hours. The solution was diluted with pentane (20 mL), and the mixture was then filtered through a pad of celite. The filtrate was concentrated, and the residue was distilled under reduced pressure to give 3.0 g (43%) of (4R,5R)-2-allyl-2-isopropenyloxy-4,5-bis-(1-methoxy-1-methyl-ethyl)-[1,3,2]dioxasilolane as a clear, colorless liquid.

(eq. XVII)

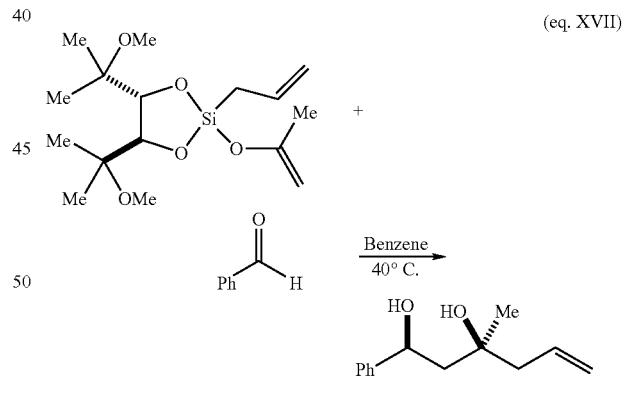

Asymmetric tandem aldol-allylation reaction of benzaldehyde to give (1S,3S)-3-methyl-1-phenyl-hex-5-ene-1,3-diol: To a solution of (4R,5R)-2-allyl-2-isopropenyloxy-4,5-bis-(1-methoxy-1-methyl-ethyl)-[1,3,2]dioxasilolane (0.75 mmol) in benzene (0.3 mL) was added benzaldehyde (0.50 mmol). The mixture was heated to 40° C. (oil bath) and stirred at that temperature for 48 hours. The solution was cooled and 1 M HCl (10 mL) was added followed by ethyl acetate (10 mL). The mixture was stirred for 20 min. The layers were separated and the aqueous layer was extracted with ethyl acetate (10 mL). The combined organic layers were washed with saturated aqueous NaHC0$_3$ (10 mL) and brine (10 mL), dried (Na$_2$SO$_4$), filtered, and concentrated. Analysis of the residue by HPLC and $^1$H NMR revealed a 5.5:1 mixture of diastereomers and an enantiomeric excess for the major product of 68%. The residue was purified by chromatography on silica gel to give (1S,3S)-3-methyl-1-phenyl-hex-5-ene-1,3-diol in 70% yield and in 68% ee.

Determination of Enantioselectivity and Absolute Configuration of Homoallylic Alcohol Products:

Allylation of Benzaldehyde with allylation reagent 3: The ee was determined by chiral HPLC analysis using a chiralcel OD column, as shown in FIG. 3. The (R) enantiomer elutes first.

Allylation of Cinnamaldehyde with allylation reagent 3: The ee was determined by chiral HPLC analysis using a chiralcel OD column, as shown in FIG. 4. The (R) enantiomer elutes first.

Allylation of Dihydrocinnamaldehyde with allylation reagent 3: The ee was determined by chiral HPLC analysis using a chiralcel OD column, as shown in FIG. 5. The (S) enantiomer elutes first.

Allylation of Isovaleraldehyde with allylation reagent 3: The ee was determined by $^{19}$F NMR (C$_6$D$_6$, 282 MHz) analysis of the Mosher ester of the product, as shown in FIG. 6. The absolute configuration (R) of the alcohol product was determined by optical rotation and comparison to the literature value: $[\alpha]_D^{20}$+18.2° (CH$_2$Cl$_2$, c 0.74); literature: $[\alpha]_D^{20}$−2.5° (CH$_2$Cl$_2$, c 9.26) for the (S) enantiomer of 16% ee.

Figure 7:
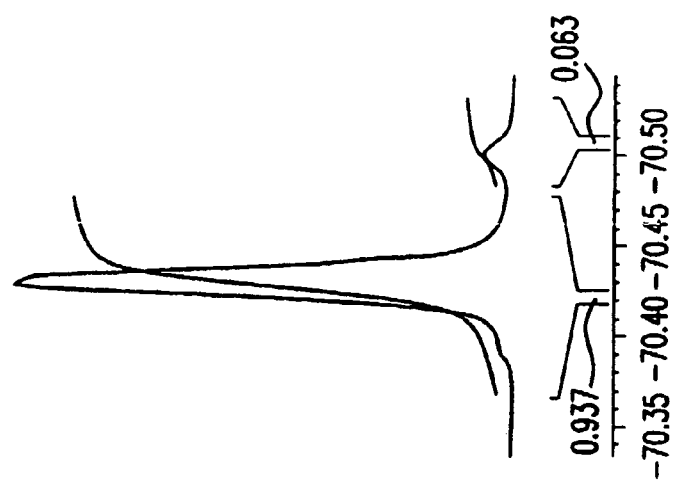
FIG. 7 shows a $^{19}$F NMR ($C_6D_6$, 282 MHz) spectrum of the Mosher ester of the alcohol obtained by allylation of cyclohexanecarboxaldehyde with allylation reagent 3 and of the corresponding racemic alcohol.
Figure 7:
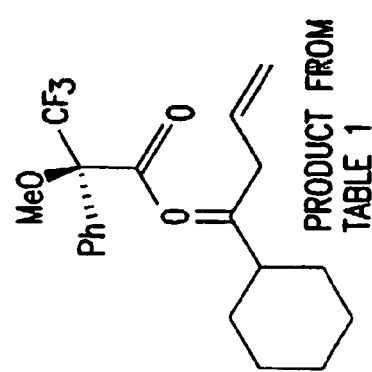
Figure 7:
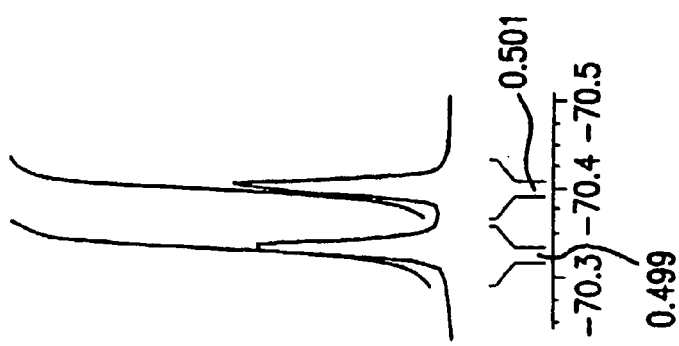
Figure 7:
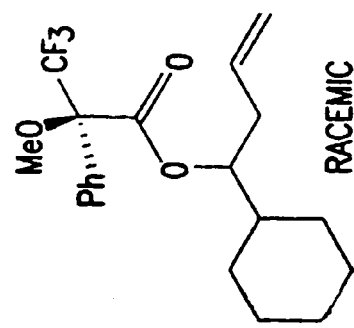

Allylation of Cyclohexanecarboxaldehyde with allylation reagent 3: The ee was determined by $^{19}$F NMR (C$_6$D$_6$, 282 MHz) analysis of the Mosher ester of the product, as shown in FIG. 7. The absolute configuration (S) of the alcohol product was determined by optical rotation and comparison to the literature value: $[\alpha]_D^{20}$−6.67° (EtOH, c 0.775); lit: $[\alpha]_D^{24}$+ 9.7° (EtOH, c 1.00) for the (R) enantiomer of 98% ee.

Allylation of Pivaldehyde with allylation reagent 3: The ee was determined by $^{19}$F NMR (C$_6$D$_6$, 282 MHz) analysis of the Mosher ester of the product, as shown in FIG. 8. The absolute configuration (S) of the alcohol product was determined by optical rotation and comparison to the literature value: $[\alpha]_D^{20}$−13.2° (PhH, c 0.28); lit: $[\alpha]_D$+10.3° (PhH, c 10.5) for the (R) enantiomer of 88% ee.

Figure 9:
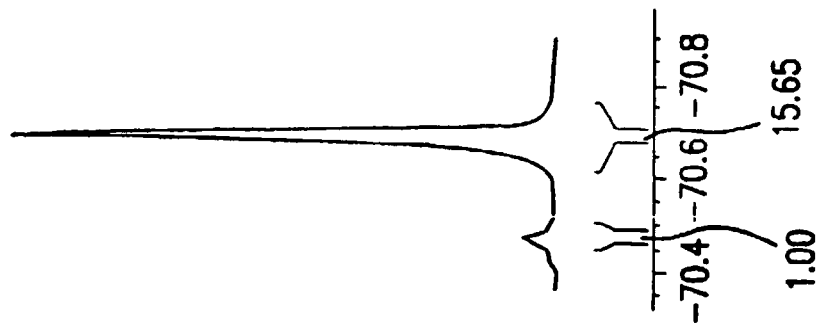
FIG. 9 shows a $^{19}$F NMR (C6D$_6$, 282 MHz) spectrum of the Mosher ester of the alcohol obtained by allylation of benzyloxyacetaldehyde with allylation reagent 3 and of the corresponding racemic alcohol.
Figure 9:
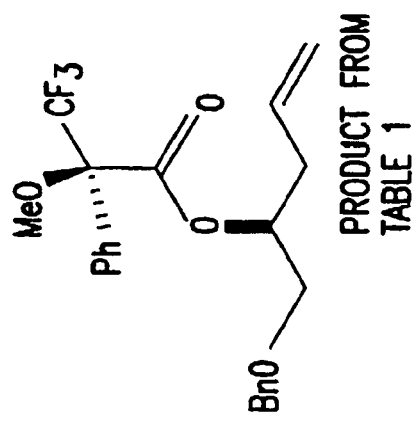
Figure 9:
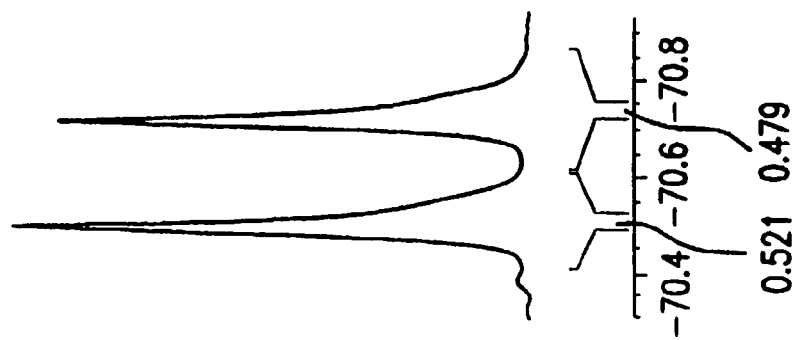
Figure 9:
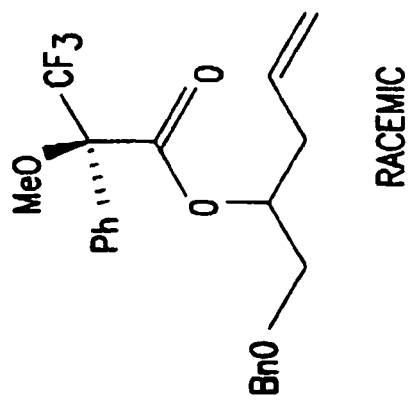

Allylation of Benzyloxyacetaldehyde with allylation reagent 3: The ee was determined by $^{19}$F NMR (C$_6$D$_6$, 282 MHz) analysis of the Mosher ester of the product, as shown in FIG. 9. The absolute configuration (S) of the alcohol product was determined by optical rotation and comparison to the literature value: $[\alpha]_D^{18}$+5.77° (CHCl$_3$, c 1.06); lit: $[\alpha]_D^{25}$− 6.6° (CHCl$_3$, c 2.1) for the (R) enantiomer of >99% ee.

Figure 10:
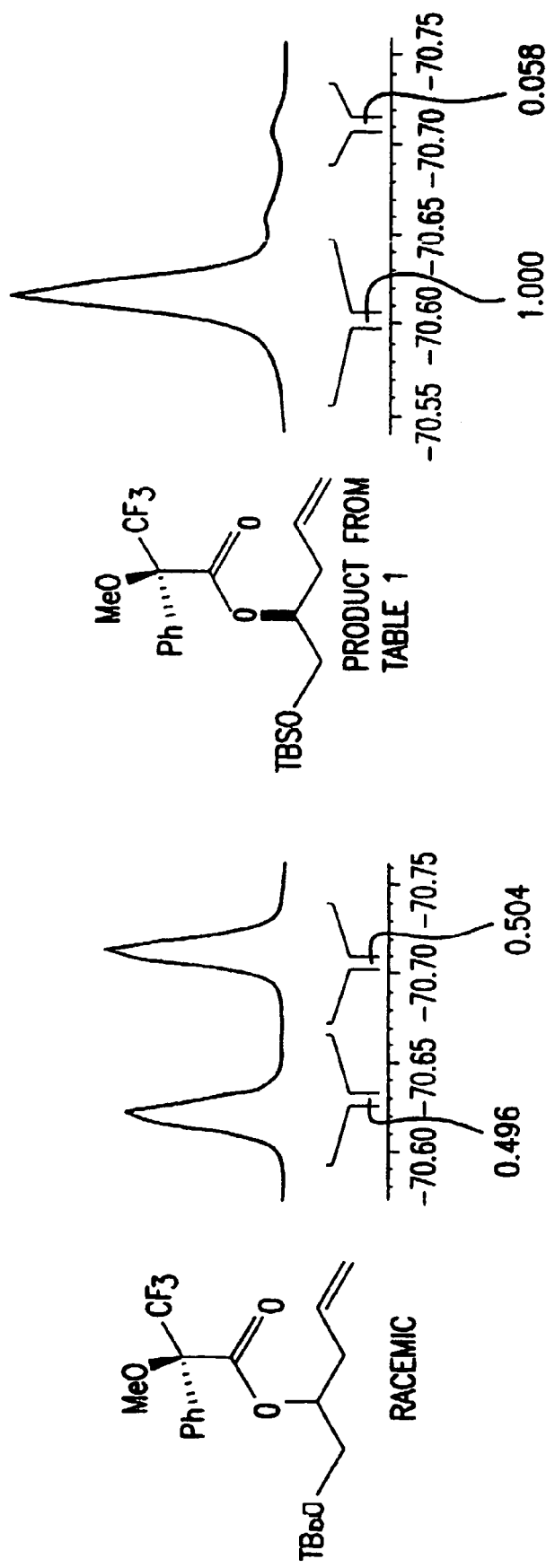
FIG. 10 shows a $^{19}$F NMR ($C_6D_6$, 282 MHz) spectrum of the Mosher ester of the alcohol obtained by allylation of tert-Butyldimethylsilyloxyacetaldehyde with allylation reagent 3 and of the corresponding racemic alcohol.

Allylation of tert-Butyldimethylsilyloxyacetaldehyde with allylation reagent 3: The ee was determined by $^{19}$F NMR (C$_6$D$_6$, 282 MHz) analysis of the Mosher ester of the product, as shown in FIG. 10. The absolute configuration (S) of the alcohol product was determined by optical rotation and comparison to the literature value: $[\alpha]_D^{20}$+1.4° (CHCl$_3$, c 1.00); lit: $[\alpha]_D^{20}$+1.7° (CHCl$_3$, c 0.24) for the (S) enantiomer of 59% ee.

Figure 12:
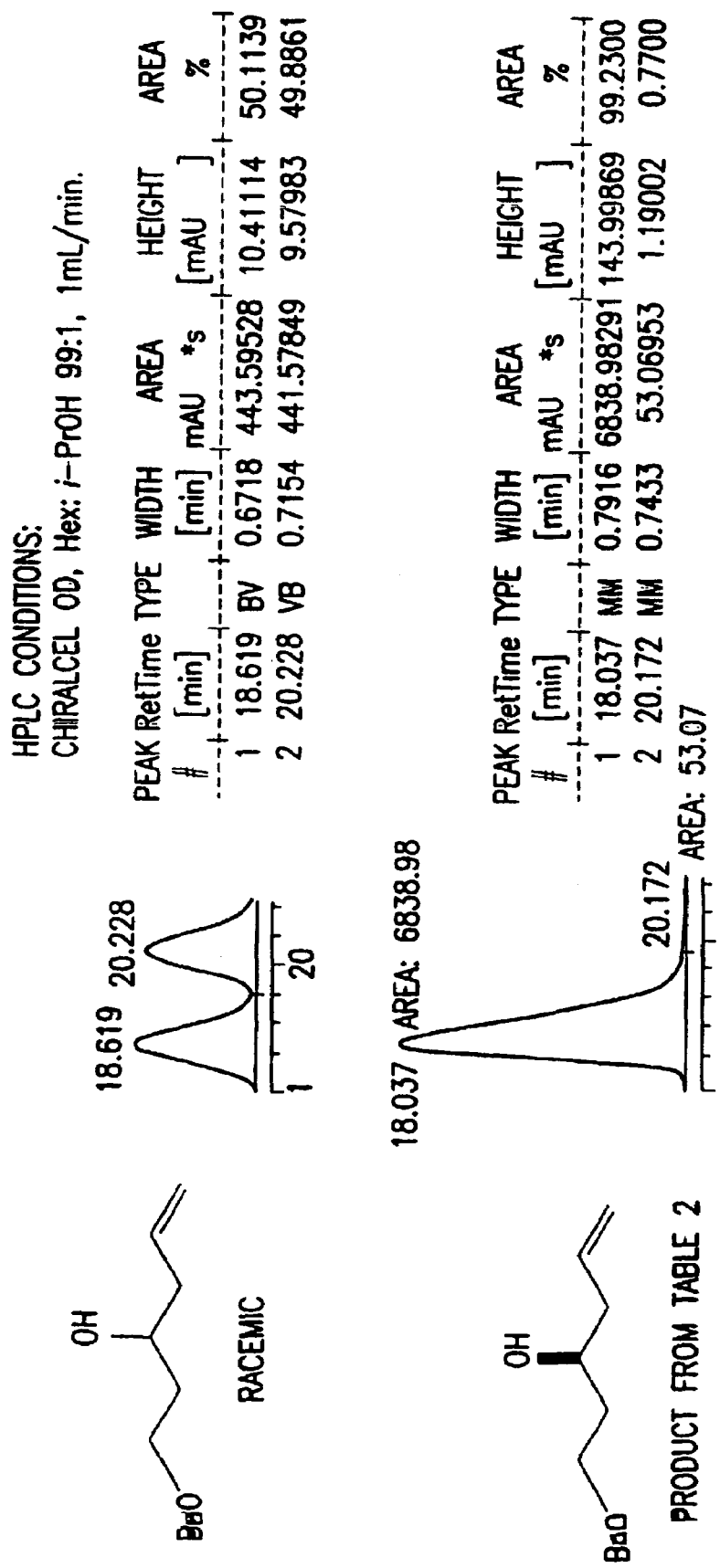
FIG. 12 shows a chiral HPLC analysis of the alcohol obtained by allylation of 3-(Benzyloxy)propionaldehyde with allylation reagent (R,R)-21 and of the corresponding racemic alcohol.

Allylation of 3-(Benzyloxy)pronionaldehyde with allylation reagent (R,R)-21: The ee was determined by chiral HPLC analysis using a chiralcel OD column, as shown in FIG. 12.

Figure 13:
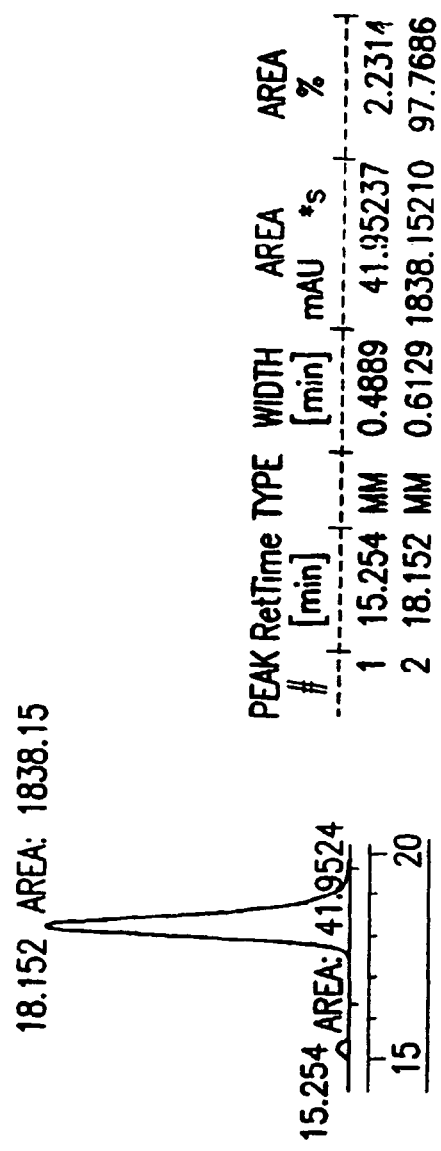
FIG. 13 shows a chiral HPLC analysis of the alcohol obtained by allylation of 3-p-anisaldehyde with allylation reagent (R,R)-21 and of the corresponding racemic alcohol.
Figure 13:
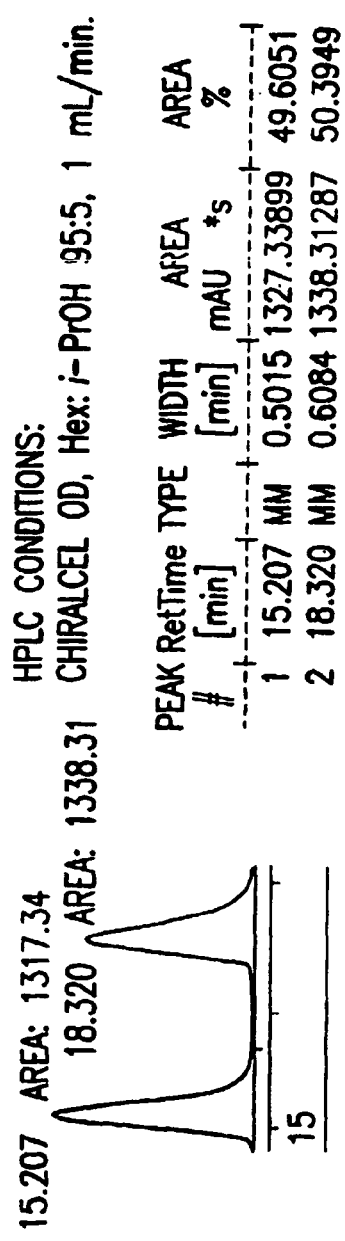

Allylation of p-Anisaldehyde with allylation reagent (R,R)-21: The ee was determined by chiral HPLC analysis using a chiralcel OD column, as shown in FIG. 13. The (R) enantiomer elutes first.

Figure 14:
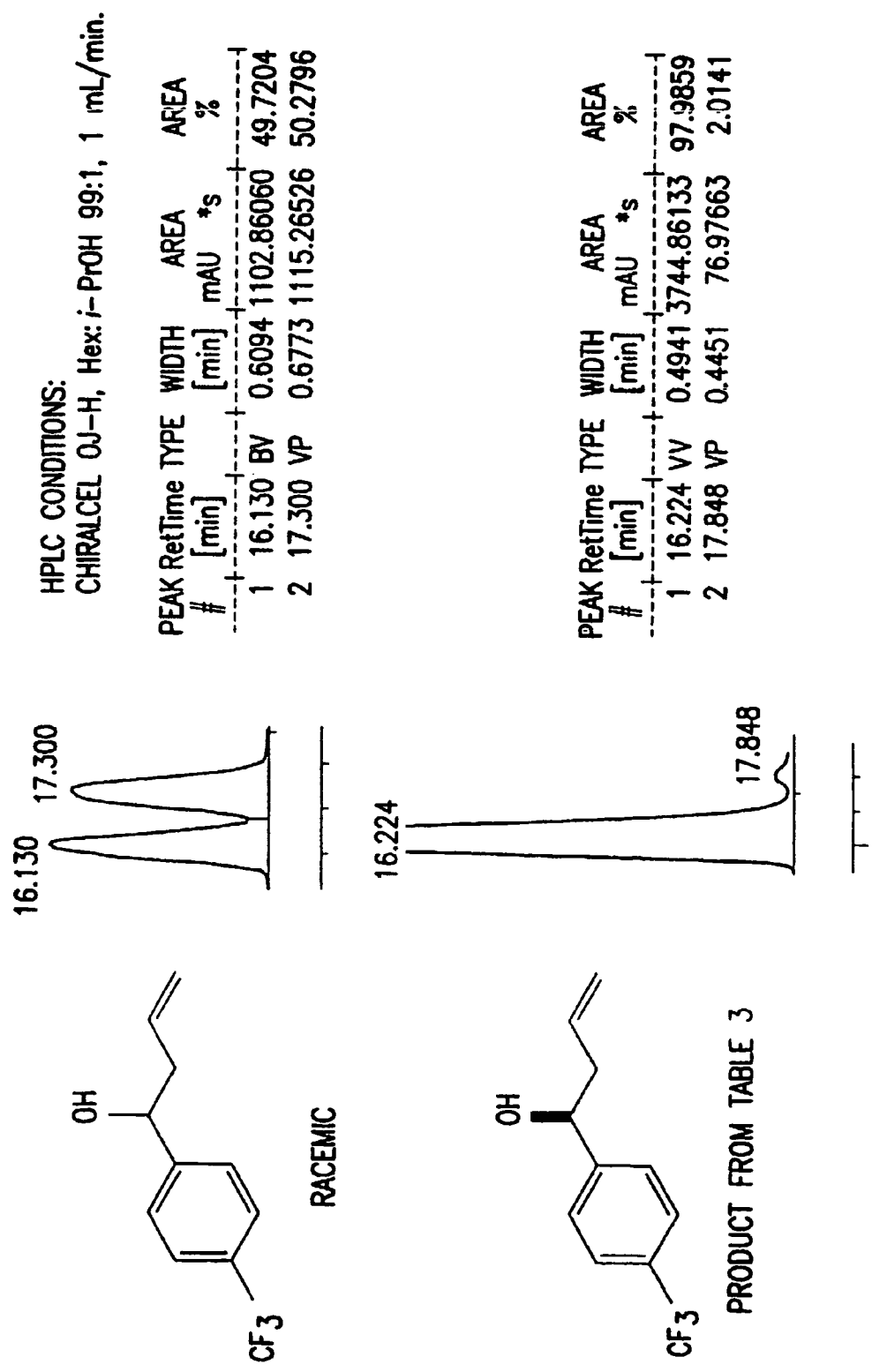
FIG. 14 shows a chiral HPLC analysis of the alcohol obtained by allylation of 3-p-CF$_3$-benzaldehyde with allylation reagent (R,R)-21 and of the corresponding racemic alcohol.

Allylation of p-CF$_3$-Benzaldehyde with allylation reagent (R,R)-21: The ee was determined by chiral HPLC analysis using a chiralcel OJ-H column, as shown in FIG. 14. The (S) enantiomer elutes first.

Figure 15:
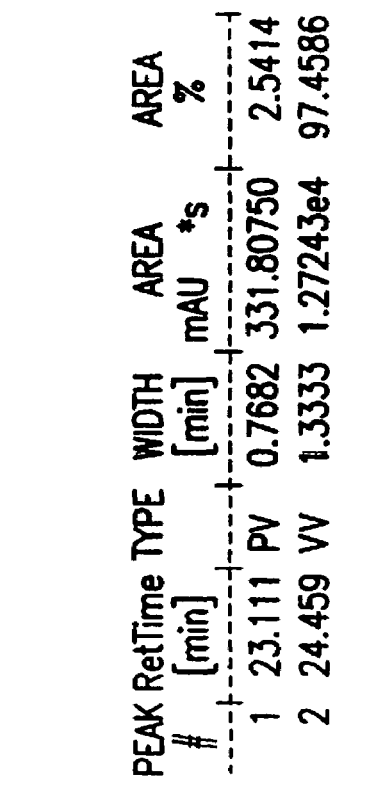
FIG. 15 shows a chiral HPLC analysis of the alcohol obtained by allylation of 3-trans-2-hexenal with allylation reagent (R,R)-21 and of the corresponding racemic alcohol.
Figure 15:
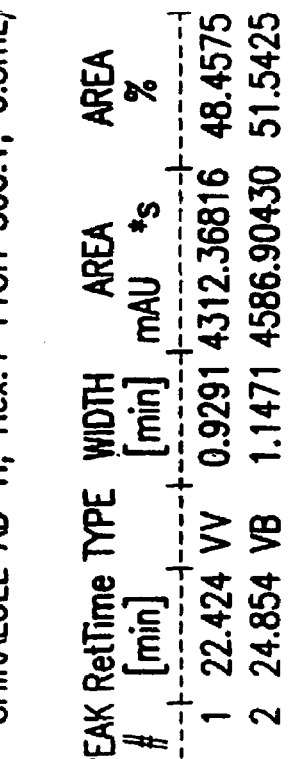
Figure 15:
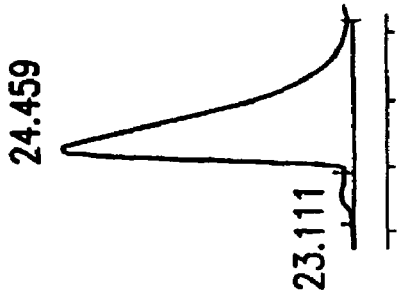
Figure 15:
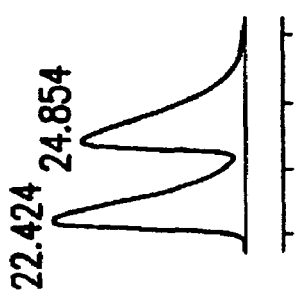
Figure 15:
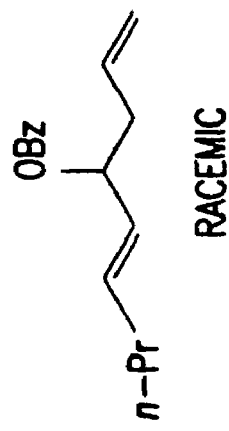
Figure 15:
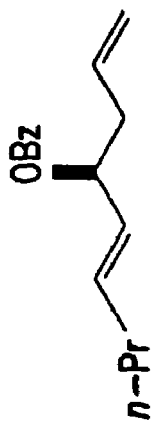

Allylation of trans-2-Hexenal with allylation reagent (R,R)-21: The ee was determined by chiral HPLC analysis of the derived benzoate using a chiralcel AD-H column, as shown in FIG. 15.

Determination of Enantioselectivity and Absolute Configuration of Products of Tandem Aldol Allylation Reactions of Cyclohexanecarboxaldehyde:

The diol having the formula

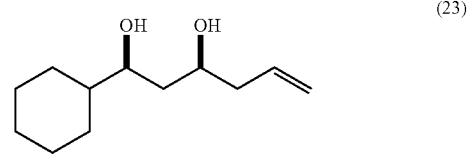

(23)

was treated with 2,2-dimethoxypropane and a catalytic amount of (+)-camphorsulfonic acid (CSA) in CH$_2$Cl$_2$ to give acetonide A (equation XVIII). The $^{13}$C NMR spectrum of acetonide A was analyzed to reveal that the acetonide possessed the syn relative configuration, establishing the syn stereochemistry of the diol.

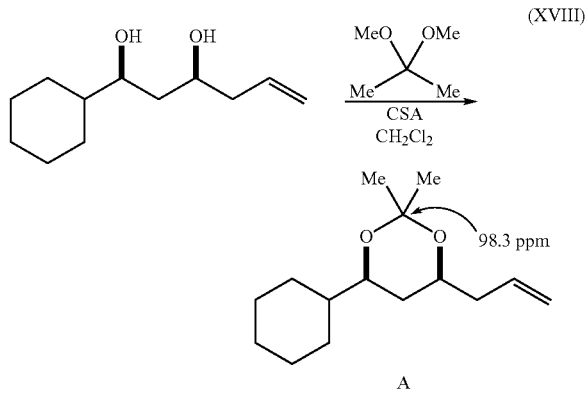

(XVIII)

Spectroscopic data for acetonide A: $^1$H NMR (400 MHz, CDCl$_3$) δ 5.85-5.72 (m, 1H, CH=CH$_2$), 5.10-4.99 (m, 2H, CH=CH$_2$), 3.85-3.77 (m, 1H, CH), 3.52-3.45 (m, 1H, CH), 2.33-2.24 (m, 1H, one of CH$_2$), 2.17-2.08 (m, 1H, one of CH$_2$), 1.92-1.83 (m, 1H, one of CH$_2$), 1.74-1.58 (m, 4H, one of CH$_2$ and three of C$_6$H$_{11}$), 1.51-0.81 (m, 8H, eight of C$_6$H$_{11}$), 1.38 (s, 3H, CH$_3$) 1.36 (s, 3H, CH$_3$); $^{13}$C NMR (100 MHz, CDCl$_3$) δ 134.4, 116.9, 98.3, 73.2, 68.8, 42.8, 41.0, 33.4, 30.2, 28.9, 27.9, 26.6, 26.1, 25.9, 19.8; IR (thin film) 3077, 2992, 2925, 2853, 1643, 1451, 1379, 1262, 1200, 1171 cm$^{-1}$.

The diol having the formula

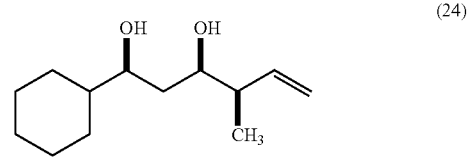

(24)

was treated with 2,2-dimethoxypropane and a catalytic amount of (+)-camphorsulfonic acid in CH$_2$Cl$_2$ to give acetonide B (equation XIX). The $^{13}$C NMR spectrum of this acetonide was analyzed to reveal that the acetonide possessed the syn relative configuration, establishing the syn stereochemistry of the diol. The relative configuration of the allylic methyl group was deduced from the sterochemistry of acetonide D, which was assigned as described below.

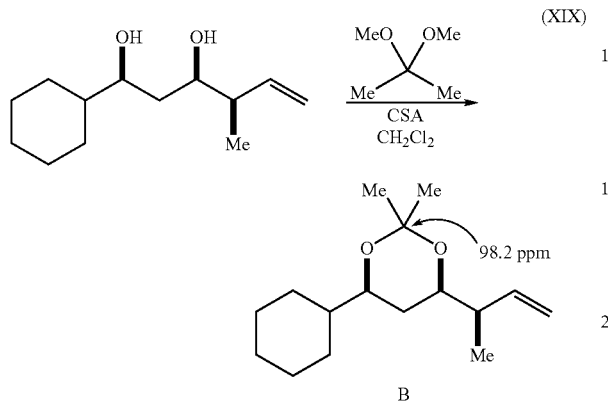

(XIX)

Spectroscopic data for acetonide B: $^1$H NMR (300 MHz, CDCl$_3$) δ 5.73-5.60 (m, 1H, CH=CH$_2$), 5.00-4.91 (m, 2H, CH=CH$_2$), 3.50-3.37 (m, 2H, two CHOC(CH$_3$)$_2$, 2.17-2.05 (m, 1H, CH(CH$_3$)CH=CH$_2$), 1.85-1.00 (br m, 13H, CH$_2$ and C$_6$H$_{11}$), 1.31 (s, 3H, one of CH$_3$), 1.30 (s, 3H, one of CH$_3$), 0.95 (d, J=6.7 Hz, 3H, CH(CH$_3$)CH=CH$_2$); $^{13}$C NMR (75 MHz, CDCl$_3$) δ 140.4, 114.7, 98.2, 73.3, 72.5, 43.5, 42.9, 31.5, 30.2, 28.9, 28.0, 26.6, 26.1, 26.0, 19.7, 15.7; IR (thin film) 3078, 2921, 2852, 1636, 1450, 1376, 1259, 1200, 1106 cm$^{-1}$.

The diol having the formula

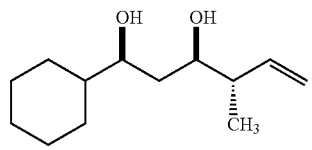

(25)

was treated with 2,2-dimethoxypropane and a catalytic amount of (+)-camphorsulfonic acid in CH$_2$Cl$_2$ to give acetonide C (equation XX). The $^{13}$C NMR spectrum of this acetonide was analyzed to reveal that the acetonide possessed the syn relative configuration, establishing the syn stereochemistry of the diol. The relative configuration of the allylic methyl group was assigned as described below.

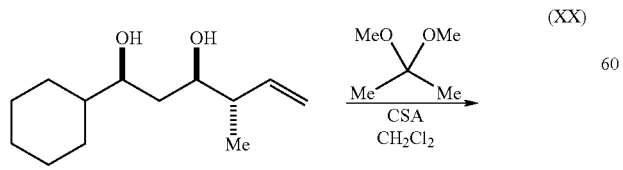

(XX)

-continued

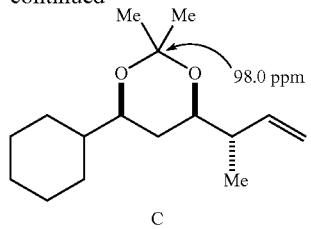

C

Spectroscopic data for acetonide C: $^1$H NMR (300 MHz, CDCl$_3$) δ 5.90-5.78 (m, 1H, CH=CH$_2$), 5.04-4.98 (m, 2H, CH=CH$_2$), 3.70-3.64 (m, 1H, one of CHOC(CH$_3$)$_2$), 3.52-3.45 (m, 1H, one of CHOC(CH$_3$)$_2$), 2.24-2.20 (m, 1H, CH(CH$_3$)CH=CH$_2$), 1.93-0.88 (m, 13H, C$_6$H$_{11}$ and CH$_2$), 1.38 (s, 3H, one of CH$_3$), 1.36 (s, 3H, one of CH$_3$), 1.00 (d, J=6.9 Hz, 3H, CH(CH$_3$)CH=CH$_2$); $^{13}$C NMR (75 MHz, CDCl$_3$); δ 140.6, 114.2, 98.0, 73.1, 72.4, 42.8, 42.4, 30.4, 30.0, 28.8, 28.0, 26.6, 26.0, 25.9, 19.6, 14.8; IR (thin film) 3078, 2921, 2852, 1636, 1450, 1376, 1259, 1200, 1106cm$^{-1}$.

Acetonide C was subjected to ozonolysis with a reductive workup with NaBH$_4$, and the resulting alcohol was treated with PPTS in CH$_2$Cl$_2$ to give acetonide D (equation XXI). Analysis of the coupling constants of D in the $^1$H NMR spectrum established the anti relative configuration of the allylic methyl group. Since acetonides B and D were both shown to have the syn diol stereochemistry and since they are different compounds, the syn relative configuration of the allylic methyl group in B and in the diol starting material is also thereby proven.

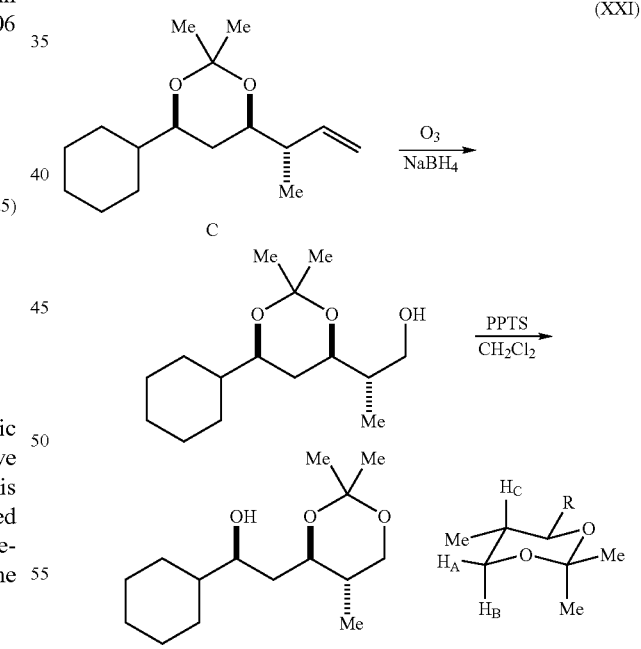

(XXI)

Spectroscopic data for acetonide D: $^1$H NMR (300 MHz, acetone-d$_6$) δ 3.75-3.67 (m, 1H, CHOC(CH$_3$)$_2$ or CHOH), 3.57 (dd, J=5.4, 11.6 Hz, 1H, one of CH$_2$OC(CH$_3$)$_2$), 3.48 (dd, J=11.0, 11.0 Hz, 1H, one of CH$_2$OC(CH$_3$)$_2$), 3.50-3.45 (m, 1H, CHOC(CH$_3$)$_2$ or CHOH), 3.36 (br s, 1H, OH), 1.83-0.98 (m, 14H, C$_6$H11, CH$_2$, and CHCH$_3$), 1.41 (s, 3H, one of CH$_3$), 1.25 (s, 3H, one of CH$_3$), 0.72 (d, J=6.7 Hz, 3H, CH(CH$_3$)); $^{13}$C NMR (100 MHz, CDCl$_3$) δ 98.2, 77.6, 76.4, 65.8, 43.9, 36.4, 34.5, 29.7, 28.9, 27.8, 26.6, 26.3, 26.2, 19.2, 12.6; IR (thin film) 3522, 2925, 1450, 1377, 1264, 1200, 1111 cm$^{-1}$.

The diol having the formula

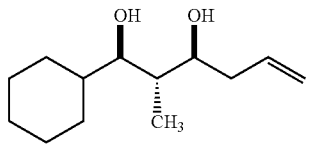

(26)

was treated with 2,2-dimethoxypropane and a catalytic amount of (+)-camphorsulfonic acid in CH$_2$Cl$_2$ to give acetonide E (equation XXII). The $^{13}$C NMR spectrum of this acetonide was analyzed to reveal that the acetonide possessed the syn relative configuration, establishing the syn stereochemistry of the diol. Analysis of the coupling constants of E, obtained from decoupling experiments, in the $^1$H NMR spectrum established the anti relative configuration of the methyl group.

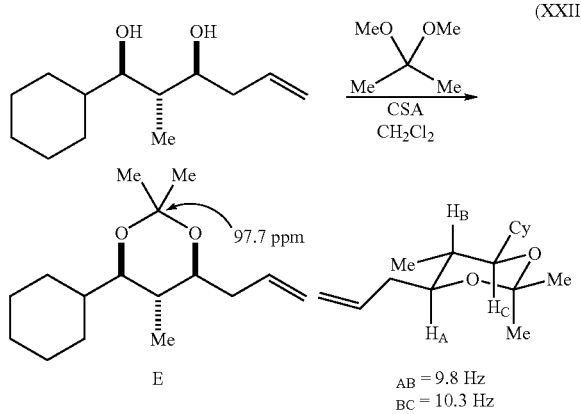

(XXII)

Spectroscopic data for acetonide E: $^1$H NMR (400 MHz, CDCl$_3$) δ 5.86-5.96 (m, 1H, CH=CH$_Z$), 5.01-5.08 (m, 2H, CH=CH$_2$), 3.50 (m, 1H, OCHCH$_2$), 3.28 (d, 1H, J=10.3 Hz, c-C$_6$H$_{11}$CHO), 2.34-2.41 (m, 1H, one of CH$_2$CH=CH$_2$), 2.13-2.21 (m, 1H, one of CH$_2$CH=CH$_2$), 1.71-1.77 (m, 2H, two of c-C$_6$H$_{11}$), 1.37 (s, 3H, three of C(CH$_3$)$_2$), 1.34 (s, 3H, three of C(CH$_3$)$_2$), 1.11-1.65 (m, 10H, CHCH$_3$ and nine of c-C6H$_{11}$), 0.74 (d, 3H, J=6.6 Hz, CHCH$_3$); $^{13}$C NMR (100 MHz, CDCl$_3$) δ 135.3, 116.1, 97.7, 77.7, 74.2, 38.4, 37.6, 34.2, 30.4, 30.1, 26.9, 26.6, 26.5, 24.8, 19.5, 11.8; IR (film) 3075, 2991, 2931, 2853, 1641, 1451, 1379, 1264, 1203, 1176, 1131, 1051, 1015, 987, 935, 910 cm$^{-1}$.

The diol having the formula

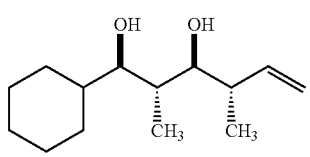

(27)

was treated with 2,2-dimethoxypropane and a catalytic amount of (+)-camphorsulfonic acid in CH$_2$Cl$_2$ to give acetonide F (equation XXIII). The $^{13}$C NMR spectrum of this acetonide was analyzed to reveal that the acetonide possessed the syn relative configuration, establishing the syn stereochemistry of the diol. Analysis of the coupling constants in the $^1$H NMR spectrum established the anti relative configuration of the methyl group between the two OH groups.

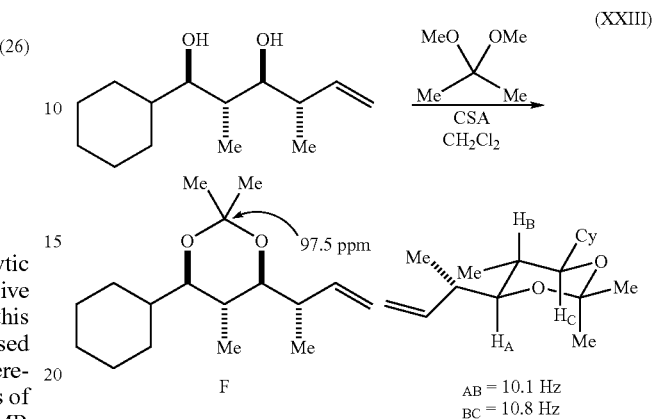

(XXIII)

Spectroscopic data for acetonide F: $^1$H NMR (400 MHz, CDCl$_3$) δ 5.96-5.82 (m, 1H, CH=CH$_2$), 5.07-4.94 (m, 2H, CH=CH$_2$), 3.35 (dd, J=10.1, 1.7 Hz, 1H, CHO), 3.28 (d, J=10.8 Hz, 1H, CHO), 2.51-2.39 (m, 1H, CH), 1.84-1.12 (m, 12H, CH and C$_6$H$_{11}$), 1.37 (s, 3H, CH$_3$), 1.34 (s, 3H, CH$_3$), 1.07 (d, J=6.9 Hz, 3H, CHCH$_3$), 0.72 (d, J=6.6 Hz, 3H, CHCH$_3$); $^{13}$C NMR (100 MHz, CDCl$_3$) δ 140.1, 114.5, 97.5, 77.8, 77.6, 39.6, 38.5, 32.4, 30.5, 30.1, 26.9, 26.6, 24.9, 19.3, 18.1 11.2; IR (thin film) 3072, 2990, 2930, 2853, 1642, 1451, 1378, 1256, 1202, 1176 cm$^{-1}$.

To establish the relative configuration of the allylic methyl group of the diol, the diol was first converted to a mixture of benzyl ethers which was treated with Hg(OAc)Cl in acetone to give terahydropyran G (equation XXIV) along with other products. Analysis of the coupling constants and NOE studies established the stereochemistry of the allylic methyl group of the diol.

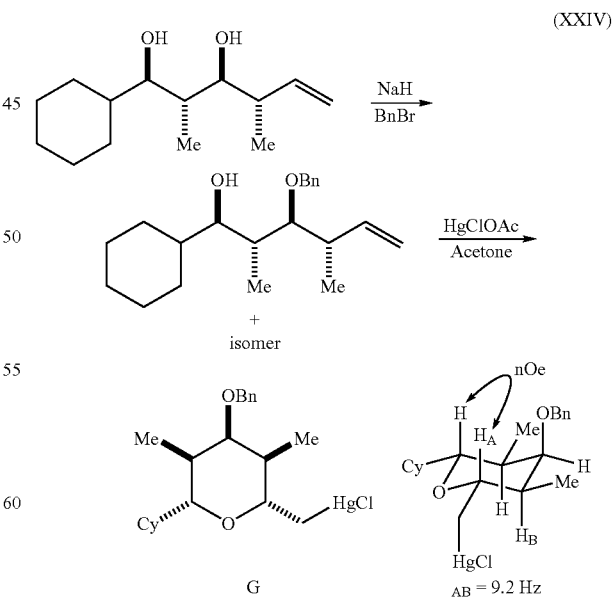

(XXIV)

Spectroscopic data for tetrahydropyran G: $^1$H NMR (400 MHz, CDCl3) δ 7.42-7.28 (m, 5H, C$_6$H$_5$), 4.69-4.61 (m, 2H, PhCH$_2$), 3.80 (ddd, J=9.8, 7.6, 4.7 Hz, 1H, CH), 3.52-3.44 (m, 2H, two CH), 2.35 (dd, J=11.7, 4.7 Hz, 1H, one of CH$_2$HgCl), 2.08 (dd, J=11.7, 7.6 Hz, 1H, one of CH$_2$HgCl), 1.85-1.13 (m, 13H, two CH and C6H$_{11}$), 1.00 (d, J=6.9 Hz, 3H, CHCH$_3$), 0.95 (d, J=7.0 Hz, CHCH$_3$); $^{13}$C NMR (100 MHz, CDCl$_3$) δ 139.0, 128.2, 127.4, 127.2, 83.4, 80.4, 75.8, 75.7, 46.1, 38.2, 38.0, 37.9, 30.9, 26.9, 26.6, 24.6, 14.5, 13.8; IR (KBr) 3025, 2930, 2855, 1654, 1607, 1450, 1376, 1337, 1193, 1095, 1067 cm$^{-1}$.

The diol having the formula

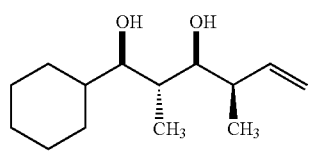

(28)

was treated with 2,2-dimethoxypropane and a catalytic amount of (+)-camphorsulfonic acid in CH$_2$Cl$_2$ to give acetonide H (equation XXV). The $^{13}$C NMR spectrum of this acetonide was analyzed to reveal that the acetonide possessed the syn relative configuration, establishing the syn stereochemistry of the diol. Analysis of the coupling constants in the $^1$H NMR spectrum established the anti relative configuration of the methyl group between the two OH groups. Since the anti allylic methyl group stereocenter of acetonide F has been established, and since the diol starting materials corresponding to acetonides F and H differ only in the allylic methyl group stereochemistry, the syn orientation of the allylic methyl group in acetonide H and in the corresponding diol starting material is therefore established.

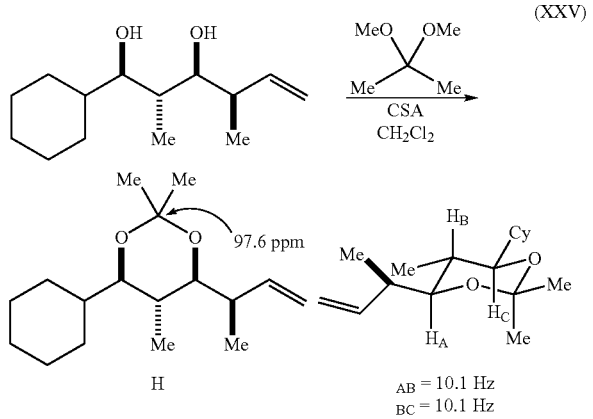

(XXV)

Spectroscopic data for acetonide H: $^1$H NMR (400 MHz, CDCl$_3$) δ 6.00-5.89 (m, 1H, CH=CH$_2$), 5.06-4.95 (m, 2H, CH=CH$_2$), 3.47 (dd, J=10.1, 2.4 Hz, 1H, CH), 3.30 (dd, J=10.1, 1.2 Hz, 1H, CH), 2.46-2.37 (m, 1H, CH), 1.83-1.11 (m, 12H, CH and C6H$_{11}$), 1.36 (s, 3H, CH$_3$), 1.33 (s, 3H, CH$_3$), 1.00 (d, J=6.9 Hz, 3H, CHCH$_3$), 0.76 (d, J=6.7 Hz, 3H, CHCH$_3$); $^{13}$C NMR (100 MHz, CDCl$_3$) δ 143.3, 112.8, 97.6, 77.9, 77.3, 38.6, 31.8, 30.5, 30.1, 26.9, 26.6, 24.9, 19.5, 12.5, 11.5; IR (thin film) 3073, 2968, 2931, 2853, 1640, 1451, 1379, 1256, 1202, 1138, 1031cm$^{-1}$.

The diol having the formula

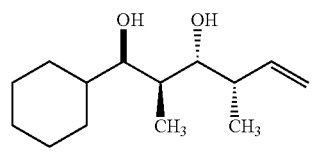

(29)

was treated with HgClOAc in CH$_2$Cl$_2$/THF to give tetrahydropyran 1 (equation XXVI). As illustrated, analysis of the coupling constants and selective 1D NOESY experiments unambiguously confirmed the relative stereochemistry of the diol.

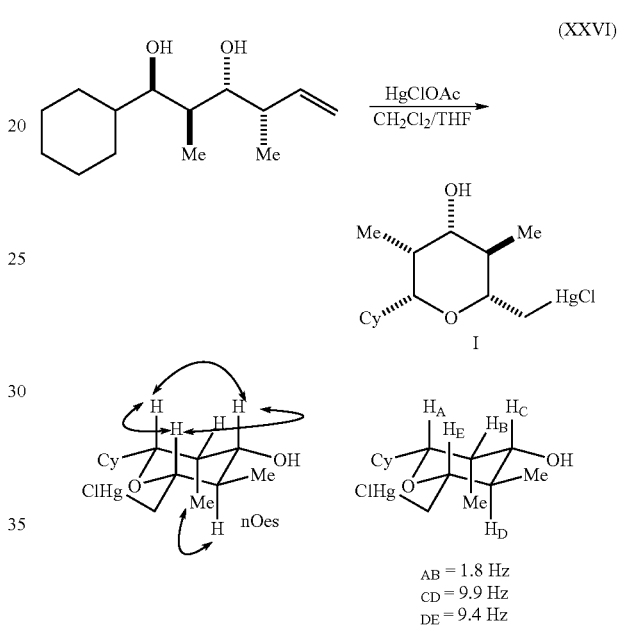

(XXVI)

Spectroscopic data for tetrahydropyran I: $^1$H NMR (400 MHz, CDCl$_3$) δ 3.40 (d, J=9.9 Hz, 1 H, CH), 3.27 (ddd, J=9.4, 8.2, 4.3 Hz, 1 H, CH), ), 3.03 (dd, J=9.7, 1.8 Hz, 1H, CH), 2.39 (dd, J=11.9, 4.3 Hz, 1 H, one of CH$_2$HgCl), 2.14 (dd, J=11.9, 8.2 Hz, 1H, one of CH$_2$HgCl), 2.16-2.07 (m, 2H, two H of C$_6$H$_{11}$), 2.07-2.98 (m, 1H, CH) 1.82-1.05 (m, 8H, CH, OH, and six H of C$_6$H$_{11}$), 0.99 (d, J=6.5 Hz, 3H, CHCH$_3$), 0.89 (d, J=6.9 Hz, 3H, CHCH$_3$), 0.94-0.75 (m, 3H, three H of C$_6$H$_{11}$); $^{13}$C NMR (100 MHz, CDCl$_3$) δ 83.53, 80.4, 42.2, 38.2, 37.3, 35.9, 30.4, 28.0, 26.5, 25.9, 25.7, 13.8, 5.7; IR (KBr) 3434, 2924, 2851, 1720, 1450, 1386, 1334, 1262, 1100, 1027 cm$^{-1}$.

We claim:

1. A compound having the formula

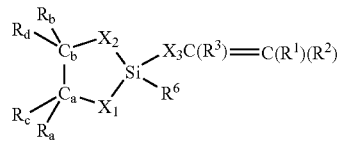

wherein $X_3$ is selected from a group consisting of O and C(R$^4$)(R$^5$);

$X_1$ and $X_2$ are N—R, or one of $X_1$ and $X_2$ is O and the other is N—R;

each of $C_a$ and $C_b$ is independently selected from the group consisting of an achiral center, an (S) chiral center and an (R) chiral center;

$R_a$ and $R_b$ are (i) each independently selected from a group consisting of $C_{1-10}$ alkyl, $C_{6-10}$ aryl, $C_{3-9}$ heteroaryl, or (ii) taken together to form a $C_3$-$C_4$ alkylene chain which together with $C_a$ and $C_b$ forms a 5-membered aliphatic ring and a 6-membered aliphatic ring;

$R_c$ and $R_d$ are each independently selected from the group consisting of hydrogen, $C_{1-10}$ alkyl, $C_{6-10}$ aryl, and $C_{3-9}$ heteroaryl;

$R^6$ is selected from the group consisting of halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{6-10}$ diarylamino, —O—C($R^9$)═C($R^7$)($R^8$), —OSO$_2$CF$_3$ and —SR;

R is selected from the group consisting of $C_{1-10}$ alkyl, $C_{6-10}$ aryl, and $C_{3-9}$ heteroaryl; and each of, $R^1$, $R^2$, $R^3$, $R^4$, $R^5$, $R^7$, $R^8$, and $R^9$ is independently selected from the group consisting of hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{6-10}$ diarylamino, and halogen.

2. The compound of claim 1, wherein $X_3$=O.

3. The compound of claim 1, wherein $X_3$=C($R^4$)($R^5$).

4. The compound of claim 1, wherein each of $R^1$, $R^2$, $R^3$, $R^4$, and $R^5$ is hydrogen, and $R^6$ is chlorine.

5. The compound of claim 1, wherein the each of $R_c$ and $R_d$ is hydrogen, each of $R_a$ and $R_b$ is 2-methoxy-2-propyl, and each of $C_a$ and $C_b$ is an (R) chiral center.

6. The compound of claim 1, wherein $X_1$=NR and $X_2$=O.

7. The compound of claim 6, wherein each of $C_a$ and $C_b$ is an (S) chiral center.

8. The compound of claim 6, wherein each of $C_a$ and $C_b$ is an (R) chiral center.

9. The compound of claim 6, wherein R is selected from the group consisting of methyl, benzyl and phenyl.

10. The compound of claim 9, wherein each of $R_a$ and $R_b$ is independently selected from the group consisting of methyl and phenyl, and each of $R_c$ and $R_d$ is independently selected from the group consisting of methyl and hydrogen.

11. The compound of claim 6 having the formula selected from a group consisting of:

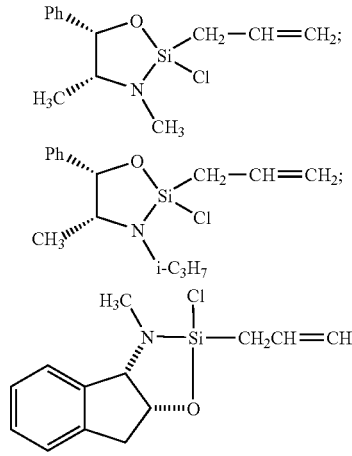

-continued

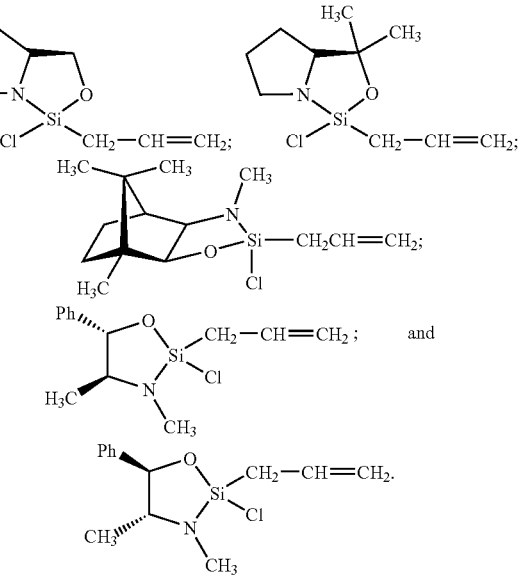

12. The compound of claim 1, wherein $X_1$=$X_2$=NR.

13. The compound of claim 12, wherein each of $C_a$ and $C_b$ is an (S) chiral center.

14. The compound of claim 12, wherein each of $C_a$ and $C_b$ is an (R) chiral center.

15. The compound of claim 12, wherein R is selected from the group consisting of methyl, benzyl and phenyl.

16. The compound of claim 15, wherein each of $R_a$ and $R_b$ is independently selected from the group consisting of methyl and phenyl, and each of $R_c$ and $R_d$ is hydrogen.

17. The compound of claim 12, wherein $R_a$ and $R_b$ are taken together to form a $C_4$ alkylene chain which together with $C_a$ and $C_b$ forms a 6-membered aliphatic ring.

18. The compound of claim 17 having the formula selected from a group consisting of:

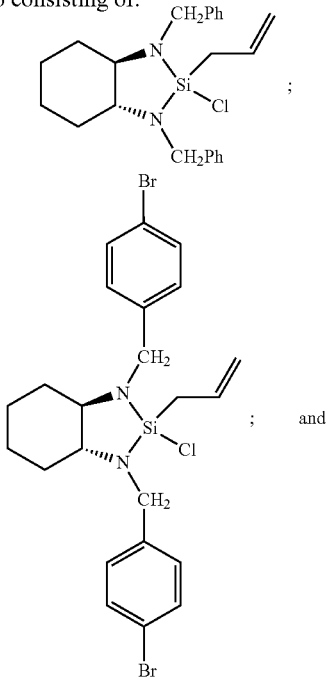

-continued

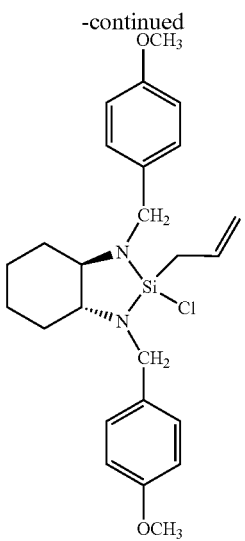

19. The compound of claim 1, wherein $R_c$ is selected from the group consisting of hydrogen, $C_{6-10}$ aryl, and $C_{3-9}$ heteroaryl.

20. The compound of claim 1, wherein $R^6$ is halogen.

21. A compound having the formula

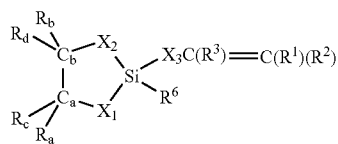

wherein $X_3$ is selected from the group consisting of O and $C(R^4)(R^5)$;

each of $X_1$ and $X_2$ is independently selected from a group consisting of O and N—R;

each of $C_a$ and $C_b$ is independently selected from the group consisting of an achiral center, an (S) chiral center and an (R) chiral center;

$R_a$ and $R_b$ are (i) each independently selected from the group consisting of $C_{1-10}$ alkyl, $C_{6-10}$ aryl, and $C_{3-9}$ heteroaryl, or (ii) taken together to form a $C_3$-$C_4$ alkylene chain which together with $C_a$ and $C_b$ forms a 5-membered aliphatic ring or a 6-membered aliphatic ring;

$R_c$ and $R_d$ are each independently selected from the group consisting of hydrogen, $C_{1-10}$ alkyl, $C_{6-10}$ aryl, and $C_{3-9}$ heteroaryl, wherein $R_a$, $R_b$, $R_c$ and $R_d$ are not methyl or phenylmethyl, wherein $R_a$, $R_b$, $R_c$ and $R_d$ are not methyl or phenylmethyl;

$R^6$ is selected from the group consisting of halogen, hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{6-10}$ diarylamino, —O—C($R^9$)=C($R^7$)($R^8$), $OSO_2CF_3$ and SR;

R is selected from the group consisting of $C_{1-10}$ alkyl, $C_{6-10}$ aryl, and $C_{3-9}$ heteroaryl; and each of, $R^1$, $R^2$, $R^3$, $R^4$, $R^5$, $R^7$, $R^8$, and $R^9$ is independently selected from the group consisting of hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{6-10}$ diarylamino, and halogen.

22. A compound having the formula

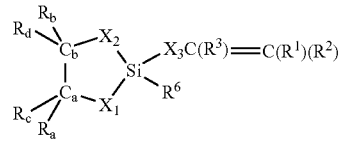

wherein $X_3$ is selected from the group consisting of O and $C(R^4)(R^5)$;

each of $X_1$ and $X_2$ is independently selected from the group consisting of O and N—R;

each of $C_a$ and $C_b$ is independently selected from the group consisting of an achiral center, an (S) chiral center and an (R) chiral center;

$R_a$ and $R_b$ are (i) each independently selected from the group consisting of $C_{1-10}$ alkyl, $C_{6-10}$ aryl, $C_{3-9}$ heteroaryl, or (ii) taken together to form a $C_3$-$C_4$ alkylene chain which together with $C_a$ and $C_b$ forms a 5-membered aliphatic ring or a 6-membered aliphatic ring;

$R_c$ and $R_d$ are each independently selected from the group consisting of hydrogen, $C_{1-10}$ alkyl, $C_{6-10}$ aryl, and $C_{3-9}$ heteroaryl;

$R^6$ is halogen;

R is selected from the group consisting of $C_{1-10}$ alkyl, $C_{6-10}$ aryl, and $C_{3-9}$ heteroaryl; and each of, $R^1$, $R^2$, $R^3$, $R^4$, $R^5$, $R^7$, $R^8$, and $R^9$ is independently selected from the group consisting of hydrogen, $C_{1-10}$ alkyl, $C_{6-10}$ aryl, $C_{3-9}$ heteroaryl, $C_{1-10}$ alkoxy, $C_{6-10}$ aryloxy, $C_{1-10}$ dialkylamino, $C_{1-10}$ alkyl-$C_{6-10}$ arylamino, $C_{6-10}$ diarylamino, and halogen.

23. The compound of claim 22, wherein $R^6$ is chloride.

* * * * *

UNITED STATES PATENT AND TRADEMARK OFFICE
CERTIFICATE OF CORRECTION

PATENT NO. : 7,534,905 B2  Page 1 of 1
APPLICATION NO. : 10/504831
DATED : May 19, 2009
INVENTOR(S) : Leighton et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (314) days Delete the phrase "by 314 days" and insert -- by 587 days --

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO.      : 7,534,905 B2                                    Page 1 of 1
APPLICATION NO. : 10/504831
DATED           : May 19, 2009
INVENTOR(S)     : Leighton et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (314) days Delete the phrase "by 314 days" and insert -- by 927 days --

Signed and Sealed this

Fourth Day of May, 2010

David J. Kappos
*Director of the United States Patent and Trademark Office*